United States Patent [19]

O'Halloran et al.

[11] Patent Number: 5,534,542

[45] Date of Patent: Jul. 9, 1996

[54] METHODS AND MATERIALS RELATING TO A BI-METALLIC CROSS-LINKING SPECIES

[75] Inventors: Thomas V. O'Halloran, Kenilworth, Ill.; Stephen P. Watton, Waltham, Mass.

[73] Assignee: Northwestern University, Evanston, Ill.

[21] Appl. No.: 187,389

[22] Filed: Jan. 24, 1994

[51] Int. Cl.$^6$ .......................... A61K 31/28; C07F 19/00; C07F 15/00; C07F 3/10

[52] U.S. Cl. .................. 514/492; 514/6; 514/501; 514/496; 556/28; 556/136; 556/137

[58] Field of Search .................. 556/136, 137, 556/28; 514/6, 492, 501, 496

[56] References Cited

U.S. PATENT DOCUMENTS

| | | | |
|---|---|---|---|
| Re. 33,071 | 9/1989 | Stjernholm | 530/394 |
| 4,310,515 | 1/1982 | Granatek et al. | 424/131 |
| 4,863,898 | 9/1989 | Ashmead et al. | 514/6 |

OTHER PUBLICATIONS

Brauman, "Bioinorganic Chemistry," *Science*, 261:663, 1993.

Abrams, M. J. and Murrer, B. A., "Metal Compounds in Therapy and Diagnosis", *Science*, 261:725–730, 1993.

Karlin, Kenneth D., "Metalloenzymes, Structural Motifs, and Inorganic Models," *Science*, 261:701–708, 1993.

O'Halloran, Thomas V., "Transition Metals in Control of Gene Expression," *Science*, 261:715–725, 1993.

Pyle, Anna Marie, "Ribozymes: A Distinct Class of Metalloenzymes," *Science*, 261:709–714, 1993.

Wright et al., "Mercury(II)–Thiolate Chemistry and the Mechanism of the Heavy Metal Biosensor MerR," *Progress in Inorganic Chemistry Bioinorganic Chemistry*, 38:323–412, 1990.

Abrams et al., Science, vol. 261, pp. 725–730 (1993).

Bonati et al., Can. J. Chem., vol. 57, No. 5, pp. 483–486 (1979).

*Primary Examiner*—Porfirio Nazario-Gonzales
*Attorney, Agent, or Firm*—Arnold, White & Durkee

[57] ABSTRACT

Disclosed herein is a bi-metallic cross-linking reagent according to the following formula:

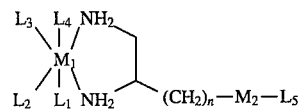

where $M_1$ is a metal ion species capable of forming a complex of coordination number four or coordination number six; wherein $L_1$, $L_2$, $L_3$, and $L_4$ are each independently a halide, ammonia, dimethyl sulfoxide, carboxylate, thiolate, imidazole, a nucleobase, or an empty coordination site, provided that no more than two of $L_1$, $L_2$, $L_3$, and $L_4$ are empty coordination sites; wherein $M_2$ is a metal ion species capable of forming a complex of coordination number two with a first ligand that is a hydrocarbon moiety and a second ligand that is kinetically lablie; and wherein n is an integer from two to nine. Also disclosed are cross-linked species, methods of preparing the crosslinking reagents of the invention, and methods for their use in tissue-specific targeting of anti-tumor agents.

32 Claims, 13 Drawing Sheets

JM-216

ZENIPLATIN

CARBOPLATIN

TETRAPLATIN

CISPLATIN

ENLOPLATIN

A

B

+

+

METHODS AND MATERIALS RELATING TO A BI-METALLIC CROSS-LINKING SPECIES

TECHNICAL FIELD OF THE INVENTION

The present invention relates in general to species for the reversible cross-linking of DNA and protein molecules, and methods pertaining to their preparation and use.

BACKGROUND OF THE INVENTION

The isolation and characterization of DNA-binding proteins which function as regulators of genetic processes is a central theme in molecular biological research. Since the vast majority of these protein factors recognize and bind to highly specific DNA sequences, this property has frequently been exploited as a means for identification of the target protein in exploratory assays. Disclosed herein is the development of a class of reagents (see FIG. 1) which are expected to enhance the utility of this approach, by acting as efficient and specific reversible DNA-protein cross-linkers. The reagents exhibit utility in the isolation of a wide variety of DNA-binding proteins. Furthermore, a major application of the cross-linking reagents of the present application will be in the study of proteins which naturally bind metal ions as an integral part of their function. Examples of these include the metalloregulatory proteins (O'Halloran, 1989), and proteins which bind to DNA via the zinc finger (Berg, 1989; Klug, 1989) and related motifs.

Reversible crosslinking of transcription factors to their DNA recognition sequences is expected to greatly facilitate the identification of this important class of proteins (Chu and Orgel, 1992). Incorporation of two discrete metal centers into a bifunctional reagent is intended to enhance the specificity of the reagent for mediation of protein-DNA crosslinks relative to non-productive side-reactions such as DNA-DNA crosslinking, which occurs extensively with simple complexes such as trans-DDP (Ciccarelli et al, 1985; Sherman & Lippard, 1987). The reagent is expected to be especially effective in the crosslinking of transcription factors that bind to DNA via metallopeptide structures such as the 'copper fist' of the ACE 1 (CUP1) metalloregulatory protein, (refs **Hamer & Karin) and the zinc-finger motifs found extensively in eukaryotic transcription factors. (Rebek & Nemeth, 1985;, Waters et al., 1978).

Crosslinking strategies have found wide application in studies of the interactions between biological molecules (Angelov, 1988; Czichos et al, 1989; Meffert & Dose, 1988; Miller & Costa, 1988; Schimmel & Budzig, 1977; Strniste & Smith, 1974; Wick & Matthews, 1991). However, the reagents designed for these studies have in almost all cases introduced the cross-links by formation of covalent carbon-carbon or carbon-heteroatom bonds. A number of disadvantages are inherent to these organic-based strategies. For example, the protocols typically require the introduction of highly reactive species, either by addition of a reactive chemical such as formaldehyde, (Renz, 1983; Renz & Kurz, 1984) or the in situ generation of a reactive intermediate through photochemical reactions (Meffert & Dose, 1988; Wick & Matthews, 1991, Frantz & O'Halloran, 1989; Peak et al., 1987). Because of the extreme reactivity of these species, the specificity of the reactions tends to be fairly limited. A second problem is that the chemical bonds mediating the cross-links are usually stronger than the linkages within the individual target biopolymers (i.e. peptide bonds or phophodiester linkages). Reversal of the cross-links is consequently difficult to achieve while maintaining the structural and functional integrity of the target molecules. In this latter regard, some improvement in reversibility has been accomplished by incorporation of a readily cleavable function such as a disulfide bond or vicinal diol into the cross-linker reagents (Kamp, 1988), but use of these reagents nevertheless results in the irreversible modification of the molecules of interest (Mauk & Mauk, 1989).

The manipulation of inorganic reactivity presents a solution to this problem. Many metal ions are capable of forming very strong coordinate bonds with the ligands present in proteins and nucleic acids, and metal ion-mediated cross-linking reactions have been reported in a number of instances (Miller & Costa, 1988; Mauk & Mauk, 1989; Ciccarelli et al, 1985; Kasselouri & Garoufis, 1990; Kosti'c, 1988; Miller & Costa, 1989). However, despite the very high formation constants which are frequently observed in certain coordination complexes of this sort, the coordinate bonds of a select group of metal complexes, particularly those of Hg(II), are nevertheless kinetically labile in some cases, and consequently are susceptible to competition by other ligands (Basolo & Pearson, 1960). Because they exhibit this combination of thermodynamic stability and kinetic lability, judicious selection of coordination complexes with the necessary thermodynamic and kinetic properties can provide the basis for crosslinking strategies which require the formation of very strong but reversible linkages.

The high affinity of complexes of the late transition metals for biological ligands such as the aromatic nitrogen atoms of the nucleobases and sulfur-containing sidechains in proteins has been exploited for the formation of strong covalent crosslinks in several in vivo studies. This application of transition metal chemistry has the major advantage that while some coordinate linkages are very stable, they can be nevertheless susceptible to exchange reactions with competing ligands, providing a means for reversal under mild conditions which do not cause the disruption of the biopolymer structures or leave residual covalent modifications.

Metalloregulatory Proteins

Proteins that transduce transition metal signals into changes in gene expression are said to have a metalloregulatory function. Transition metal signals can involve a change in intra- or extracellular concentration of a metal ion or metal-ligand complex, such as heme. Metalloregulatory proteins are then a subset of regulatory proteins that act, at the physiological level, as components of metal-responsive genetic switches (O'Halloran, 1989). In the broadest sense, a metalloregulatory protein can serve a sensory or regulatory role in a switching mechanism. In some cases, a single protein plays both roles.

Metal-containing regulatory proteins can capitalize on the rich variety of coordination geometries and ligand exchange rates of metal centers. The latter can serve as binding sites for small diffusible ligands, such as dioxygen, nitric oxide, superoxide, and ammonia, that constitute a biological signal.

A majority of metalloproteins involved in gene expression may not have functional roles in transducing inorganic signals or monitoring changes in metal ion concentrations. For instance, the function of zinc finger proteins may not involve changes in Zn(II) occupancy. In such cases, the metal center may simply be a ubiquitous and available cofactor whose only function is to maintain, under all physiological states, a constant three-dimensional structure for the protein. In such proteins, the coordination environment may only perform functions similar to a disulfide cross-link or a hydrophobic packing interaction. On the other hand, metal ion coordination may be a well-controlled posttranslational modification that is part of a functional switch in cellular mechanism and thus analogous to phosphorylation or $C_a^{2+}$-responsive networks.

Extensive genetic, enzymatic, and inorganic studies of bacterial mercury resistance proteins (encoded by the mer genes) provide the first comprehensive picture of tightly regulated metal-detoxification mechanism. The central theme is mercuric ion reductase, a structurally characterized flavoenzyme that reduces Hg(II) to the volatile $Hg^0$ form. The energy-dependent uptake system can deliver other heavy metal ions to the reductase, but only the mercuric ion can be detoxified by reduction to a volatile state; Ag(I), Au(I), and Cd(II) inhibit the enzyme.

The transcriptional switching mechanism centers on MerR, a protein evolved to discriminate readily between Hg(II) and other metal ions with similar coordination properties. As a receptor, MerR is sensitive to nanomolar concentrations of Hg(II) and exhibits a high degree of selectivity. Gratuitous inducers, such as Cd(II) and Zn(II), can activate transcription only when their concentration levels exceed micromolar levels (Ralston & O'Halloran, 1990).

Physical studies of stoichiometric Hg-MerR, Zn-MerR, and Cd-MerR complexes provide evidence for the molecular basis of both the sensitivity and selectivity of the metal binding site. These data are consistent with a trigonal (but not linear) mercuric thiolate environment in Hg-MerR (Watton et al, 1990), similar to that in several model complexes.

An unusual mechanism for transcriptional activation has been described for MerR (Frantz & O'Halloran, 1990). The Hg-MerR-DNA complex apparently stimulates RNA polymerase activity at the mercury-responsive promoter through an allosteric modulation of DNA structure (Heltzel et al, 1990). Both MerR and Hg-MerR bend DNA; however, the latter stabilizes a localized distortion of the DNA that is underwound by at least 30° more than in the repressed state. This signal-responsive conformation change makes the DNA a better template for RNA polymerase. Other DNA binding proteins, such as the cyclic-adenosine monophosphate receptor protein (CAP), bend or twist DNA, but these distortions do not directly stimulate transcription.

Zinc-Finger Proteins

It has been proposed that a large number of eukaryotic regulatory proteins are likely to bind to DNA through the so-called zinc-finger motif, a short polypeptide sequence containing a high frequency of cysteine and histidine residues (Berg, 1989). This motif represents a high affinity site for binding within close proximity to the DNA helix of an organomercurial species such as that incorporated in the cross-linking reagent of the present invention. Similarly, other metal-binding motifs are being recognized in metal-loregulatory proteins, such as the copper fist motif of the ACE1 protein (Welch et al., 1989; Thiele, 1988), and the mercury binding site of the MerR metalloregulatory protein. Use of the cross-linking reagent of the present invention will greatly facilitate the isolation of a variety of DNA-binding proteins, particularly, but not limited to, those gene regulatory proteins which bind to metal ions as a part of their functional requirements, such as the metalloregulatory proteins. (O'Halloran, 1989).

Zinc is a ubiquitous component of chromatin, enzymes involved in transcription (Vallee & Falchuk, 1992), and accessory transcription factors that relay a variety of intra- and intercellular signals to the nucleus and the transcriptional apparatus (Coleman, 1992). Physiological and biochemical studies have suggested an equally wide array of metalloprotein functions. The three-dimensional structures of several Cys-rich zinc binding domains involved in DNA recognition are known; these metal binding domains can also mediate protein-protein interactions (Berg & Lippard, 1989), vol. 37, p. 143). Because the gross structural features of domains within a protein can be readily achieved through peptide secondary structures without resort to cofactors such as zinc, a question concerning the physiological function of zinc occupancy arises.

The importance of small metal-organized protein domains that chelate zinc ions through two Cys and two His side chains was first suggested for the Xenopus transcription factor IIIA (TFIIIA) (Miller, 1985). The structures of several of these zinc-organized domains have been elucidated with two-dimensional NMR methods and x-ray crystallography. Zinc plays a key role in three of the seven structurally characterized classes of DNA binding domains (Harrison, 1991 ). In contrast to the MT's, which lack aromatic side chains, these zinc-stabilized domains use hydrophobic interactions in concert with the coordinate covalent Zn-S and Zn-N bonds to stabilize local protein structure. Recent x-ray crystallographic studies of the Zif268 protein reveal that three TFIIIA-like zinc fingers together can specifically recognize a 9-base pair sequence of duplex DNA with each zinc finger domain contacting two base pairs within each 3-base pair subsite. A similar mode of recognition is likely for SP1 and TFIIIA interaction with DNA. The zinc coordination sphere in these finger domains has a net electrostatic charge of zero, and one of the histidines bound to zinc in the central finger forms a hydrogen bond to a phosphate oxygen in the DNA backbone. The shortest distance between a zinc center and phosphate oxygen is about 5 Å. Of the three classes of zinc motifs discussed here, the zinc centers of Zif268 make the closest approach to the DNA backbone.

Two other structural classes of metal-organized DNA binding domains are represented by the binuclear zinc center in GAL4 and a loop-helix domain of the glucocorticoid receptor. In both cases, the stereochemistry at the zinc centers is approximately tetrahedral. As with the Zif268 crystal structure, these two zinc-peptide-DNA complexes represent a large class of homologous domains found in other transcription factors. Several other motifs consisting of some repetition of Cys and His residues within a short stretch of peptide have ben shown to mediate sequence-specific binding to DNA. It has been estimated that genes encoding "zinc finger" proteins could account for as much as 8% of chromosome 19 (Rhodes & Klug, 1993). Because other metals can bind to the Cys and His sidechains of these proteins, zinc may not be the operative metal in some of these cases.

Cisplatin and Related Anti-Tumor Agents

The observation of the inhibition of bacterial division by cisplatin formed during electrolysis experiments with platinum electrodes in nutrient media (Rosenberg et al., 1965) led to the antiproliferative effects of the compound being applied to therapy of human tumors, and today platinum drugs are among the most active and widely used clinical agents for the treatment of advanced cancer. In testicular cancer, the addition of platinum drugs to treatment regimes has led to a dramatic increase in survival rate: before cisplatin was available, only about 5% of patients were cured; today 80–90% of patients can expect long-term disease-free survival. Platinum drugs also have clinical utility in the treatment of ovarian, bladder, head and neck, and small-cell lung cancer, and combination with other agents in these types of disease is still being explored.

Structurally, the platinum compounds represent a complex formed by a central atom of platinum, surrounded by various arrangements of chlorine atoms or ammonia groups in either a cis or trans planar relationship. The diamminedichloride complex can be synthesized according to the reaction of Kauffman (Kauffman, 1963).

The ultimate target for platinum antitumor drugs is DNA. The interactions of these drugs with DNA have been extensively reviewed (Sundquist & Lippard, 1990), and it would appear that the Pt-GG intrastrand cross-link is a critical lesion that leads to cytotoxicity. (cf. FIG. 3.) Recently, proteins that bind to the Pt-DNA lesion have been identified that are homologous to HMG1 protein, and indeed HMG1 itself can bind to the damaged area (Pil et al., 1992). Cisplatin has activity in a variety of tumor systems including L1210, Sarcoma 180, Walker 256 carcinosarcoma, DMBA induced mammary tumors and ascitic B16 melanosarcoma. The compound is especially interesting in that it exhibits synergism with a large number of currently-used chemotherapeutic agents.

About ten other platinum analogs are currently, or have recently been, in clinical trials in various countries. (See FIG. 2.) With the exception of tetraplatin, all are Pt(II) complexes with leaving groups of reduced lability as compared with cisplatin; indeed, several have the same cyclobutane-1,1-dicarboxylate ligand as carboplatin. It is not always the case that such compounds have the same toxicity profile as carboplatin. However, as both zeniplatin [2,2-bis(aminoethyl)-1,3-propanediol-N,N')(cyclobutane-1,1-dicarboxylato-O,O') platinum(II)] and enloplatin (cyclobutane-1,1-dicarboxylato-O,O')(tetrahydro-4H-pyran-4,4-dimethanamine-N,N') platinum(II)] caused nephrotoxicity during phase I trials. Many of these compounds, and tetraplatin in particular, were selected on the basis of their activity against murine tumors that had become resistant to cisplatin. Such resistance is a major problem in the clinic, as many patients initially respond and then relapse; however, the relevance of the murine models is controversial.

BRIEF SUMMARY OF THE INVENTION

In one embodiment, the present invention contemplates a bi-metallic cross-linking reagent according to the formula below:

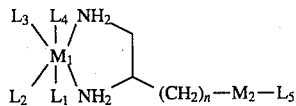

wherein $M_1$ is a metal ion species capable of forming a complex of coordination number four or coordination number six; wherein $L_1$, $L_2$, $L_3$, and $L_4$ are each independently a halide, ammonia, dimethyl sulfoxide, carboxylate, thiolate, imidazole, a nucleobase, or an empty coordination site, provided that no more than two of $L_1$, $L_2$, $L_3$, and $L_4$ are empty coordination sites; wherein $M_2$ is a metal ion species capable of forming a complex of coordination number two with a first ligand that is a hydrocarbon moiety and a second ligand that is kinetically labile; and wherein n is an integer from two to nine.

Preferably, the present invention contemplates a crosslinking reagent wherein $M_1$ is platinum, ruthenium, palladium or nickel. More preferably, the present invention contemplates a crosslinking reagent wherein up to three of $L_1$, $L_2$, $L_3$, $L_4$ and $L_5$ are each a halide, or, more preferably still, where the halide is chloride. Alternatively, the present invention contemplates a cross-linking reagent wherein $M_1$ is platinum(II), and up to two of $L_1$, $L_2$, $L_3$ and $L_4$ are empty coordination sites. More preferably, $M_1$ is platinum(IV), and none of $L_1$, $L_2$, $L_3$ and $L_4$ are empty coordination sites. Even more preferably, the present invention contemplates a cross-linking reagent wherein $M_2$ is mercury(II), and n is an integer from three to five. Alternatively, n is three or five.

In another aspect, the present invention embodies a bi-metallic nucleotide/peptide cross-linking reagent according to the following formula:

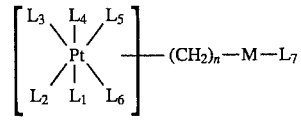

wherein $L_1$ to $L_6$ are each independently amine, a halide, cyclohexylamine, carboxylato, or empty coordination sites, provided that no more than two of $L_1$–$L_4$ are empty coordination sites; wherein any two of $L_1$ to $L_6$ are together cyclobutane-1,1-dicarboxylato-O,O', tetrahydro-4H-pyran-4,4-dimethanamine-N,N', 1,2-diaminecyclohexane-N,N', or 2,2-bis(aminomethyl)-1,3-propanediol; wherein M is a metal ion species capable of forming a complex of coordination number two with a first ligand that is a hydrocarbon moiety and a second ligand that is kinetically labile; wherein $L_7$ is a ligand that forms a kinetically labile coordination bond with M; and wherein n is an integer from 2 to 9. Preferably, the present invention embodies a cross-linking reagent of where M is mercury(II) and n is an integer from three to five.

In an alternative embodiment, the present invention encompasses a method for reversibly linking a first molecule to a second molecule, comprising the steps of (a) reacting the first molecule with the bi-metallic cross-linking reagent pictured above under conditions effective to bind a first metal ion center of the bi-metallic reagent to the molecule; and (b) reacting the product of part (a) with the second molecule under conditions effective to bind a second metal ion center of the bi-metallic reagent to the molecule. Preferably, the present invention embodies a method where the first molecule reacted is a polynucleotide and the second molecule is a protein, a peptide, or a molecule comprising a thiol moiety. However, the order of reacting the first and second molecules is immaterial to the practice of the method of the present invention and the designations of "first" and "second" molecule are for convenience in reference only. More preferably, the protein utilized in the method of the invention is a metalloregulatory protein or a protein that comprises a zinc-finger motif. More preferably still, the protein is MerR, Fur, GAL4, or TFIIIA. Alternatively, the molecule comprising a thiol moiety is a thioether, a phosphothiolate or, by way of example, hexestrol.

In yet another embodiment, the present invention discloses a linked species where a first molecule is linked to a second molecule through the bi-metallic cross-linking reagent described above, wherein the linked species is preparable by the process of (a) reacting the first molecule with the bi-metallic cross-linking reagent of claim 1 under conditions effective to bind a first metal ion center of the bi-metallic reagent to the molecule; and (b) reacting the product of part (a) with the second molecule under conditions effective to bind a second metal ion center of the bi-metallic reagent to the molecule. Preferably, the present invention discloses a linked species where a first molecule is linked to a second molecule through the bi-metallic cross-linking reagent wherein the linked species is actually prepared by the process of (a) reacting the first molecule with the bi-metallic cross-linking reagent under conditions effective to bind a first metal ion center of the bi-metallic reagent to the molecule; and (b) reacting the product of part (a) with the second molecule under conditions effective to bind a second metal ion center of the bi-metallic reagent to the molecule. More preferably, in the linked species used in the method of the present invention $M_1$ is platinum(II), $M_2$ is mercury(II), $L_2$, $L_3$, and $L_5$ are each chloride, and n is three or five. Also, the method of the present invention utilizes a second molecule that is a polynucleotide. Preferably, the first molecule is a protein, a peptide, or a molecule comprising a thiol moiety. More preferably, the protein is MerR, Fur, GAL4, or TFIIIA.

In still another embodiment, the present invention contemplates a linked species comprising a cell-specific molecule and the bi-metallic cross-linking reagent described above. Preferably, the present invention contemplates a linked species where a first metal center of the bi-metallic cross-linking reagent is linked to the cell-specific molecule and a second metal center of the cross-linking reagent comprises an anti-tumor agent. More preferably, the anti-tumor agent is selected from the group consisting of cisplatin, carboplatin, JM-216, tetraplatin, zeriplatin, and enloplatin, and the cell-specific molecule is a cell surface receptor or a nuclear receptor.

In still another embodiment, the present invention contemplates a method of delivering an anti-tumor agent to a cell where a specific cell type is targeted for delivery of the agent, the method comprising the step of administering the linked species described immediately above.

BRIEF DESCRIPTION OF THE DRAWINGS

In the drawings, which form a part of the specification.

A. Protein-binding organomercurial tethered to DNA-binding Pt(II) complex results in strong covalent crosslinks between proteins and DNA.

B. Excess of competing ligand with affinity for metal ions comparable to biopolymers results in reversal of crosslinks. Proteins and DNA are regenerated with no residual modification to side chains or nucleobases.

Figure 4:
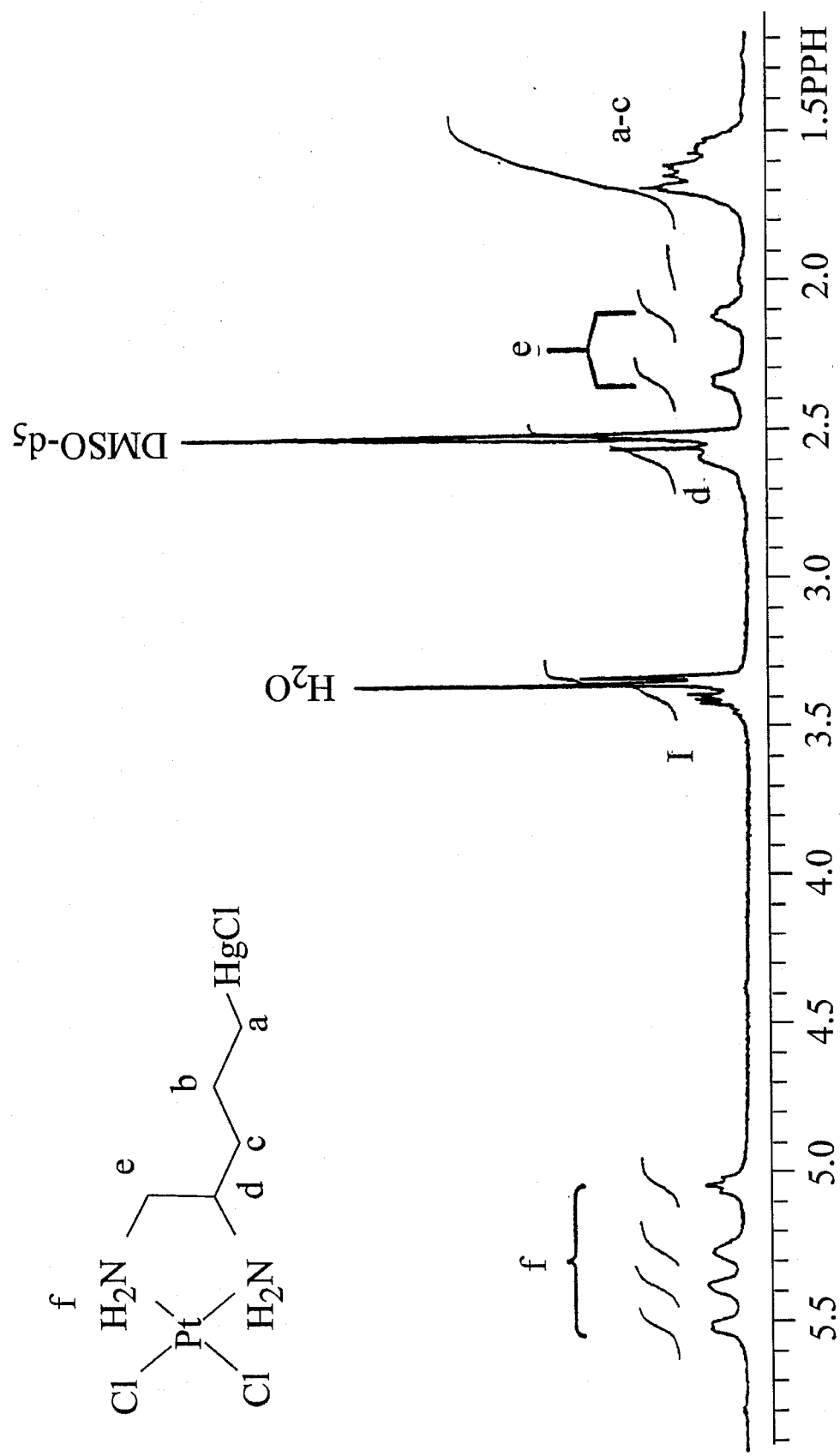

FIG. 4 is the $^1$H NMR spectrum of 5-(chloromercuri1,2-pentanediammine)dichloroplatinum(II) in $D_6$DMSO. (Reference=$d_5$-DMSO (internal))

Figure 5:
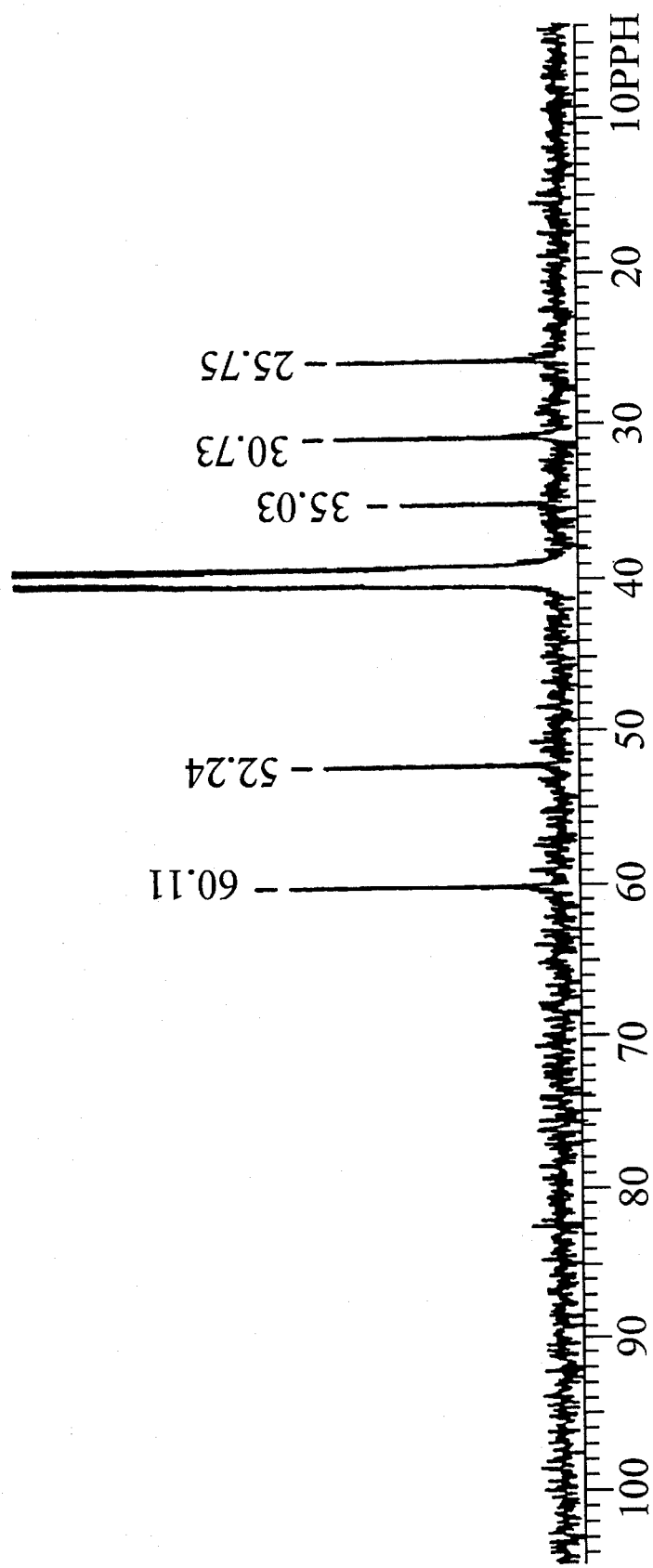

FIG. 5 is the $^1$H-Decoupled $^{13}$C NMR Spectrum of 5-(chloromercuri-1,2-pentanediammine)dichloroplatinum(II) in $d_6$-DMSO. (Reference=$d_5$-DMSO (internal))

Figure 6:
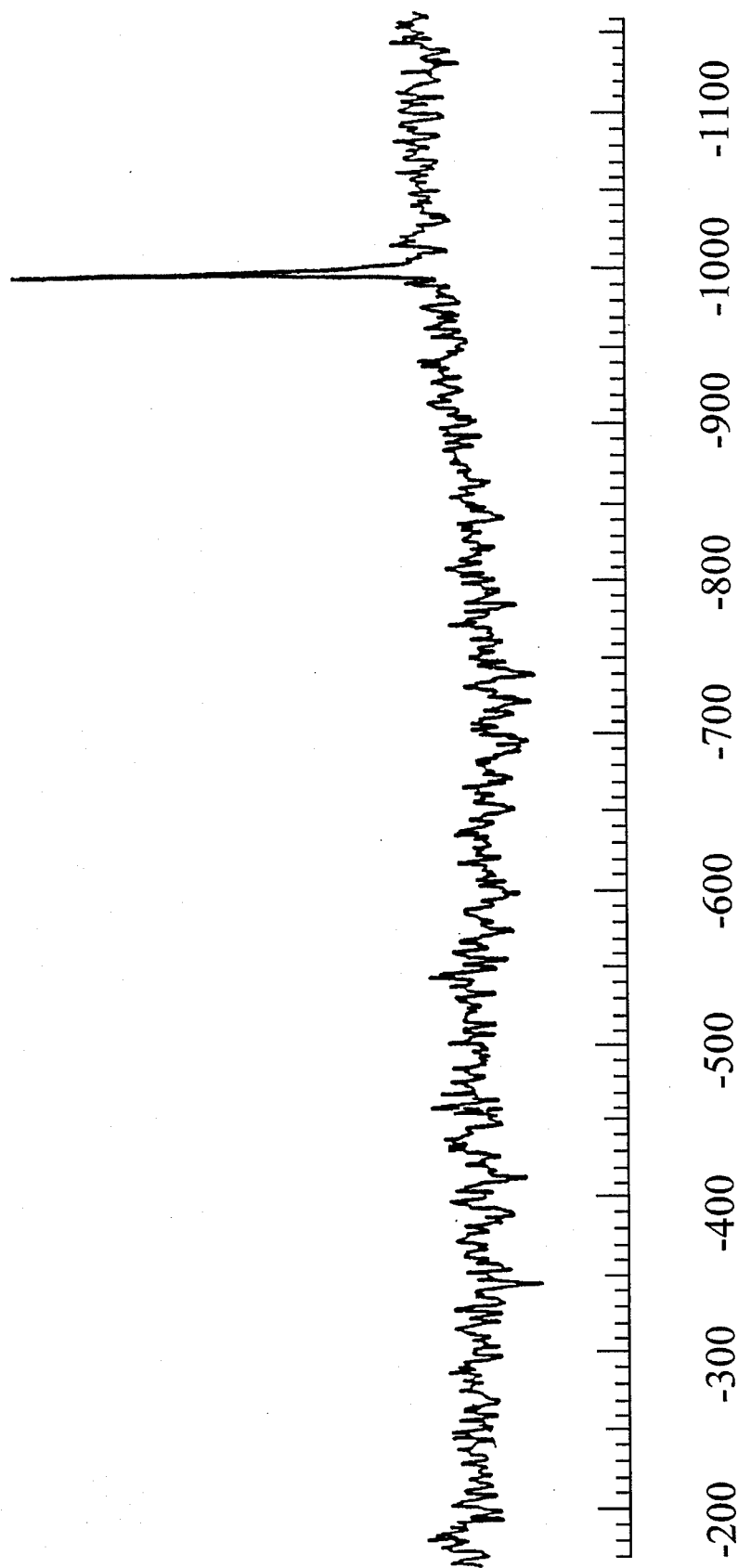
Figure 7:
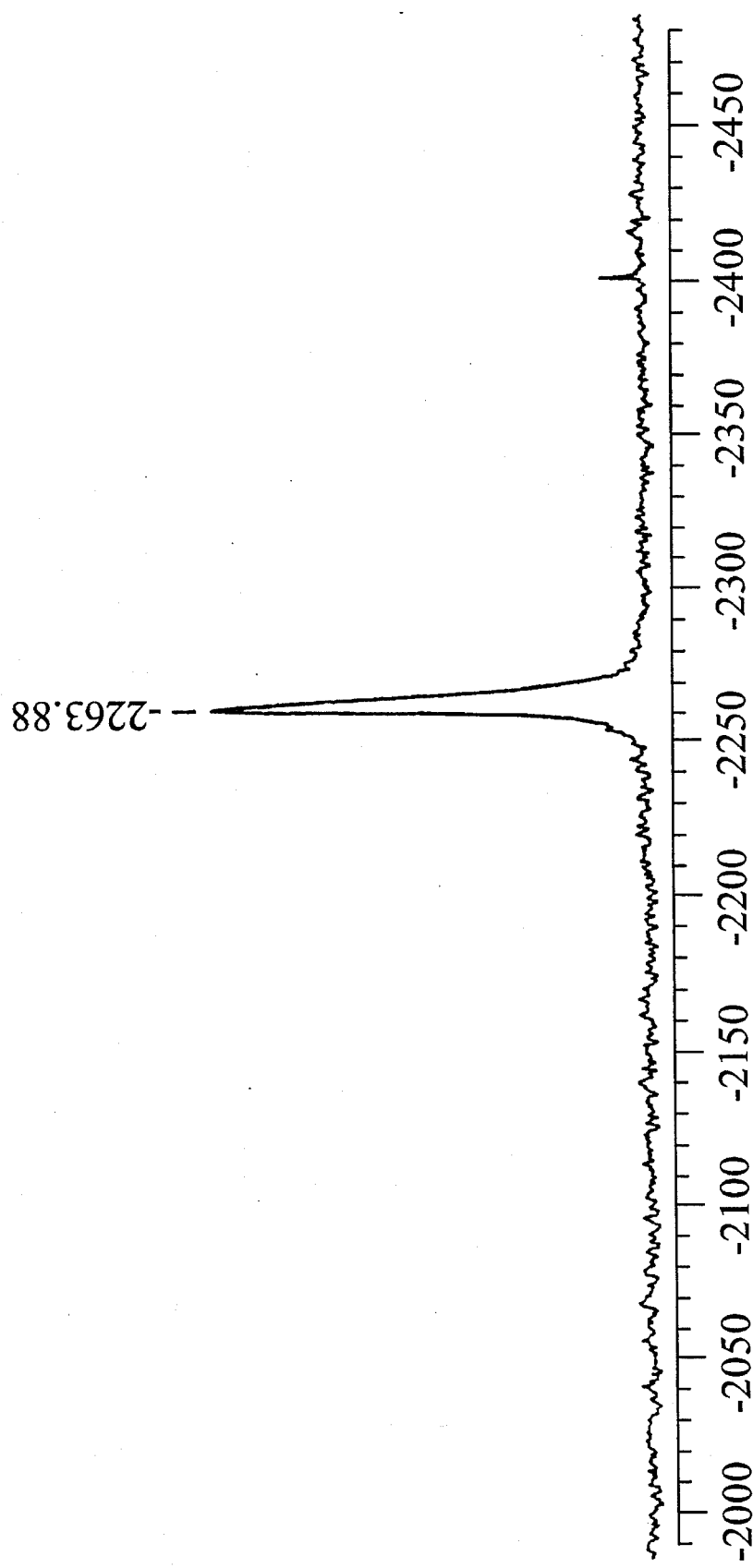

FIG. 6 is the $^1$H-Decoupled $^{199}$Hg NMR Spectrum of 5-(chloromercuri-1,2-pentanediammine)dichloroplatinum(II) in NMP; Spectral Frequency=71.600 MHz; recorded using a spectral window of 30 KHz, a pulse width of 30 μsec, and a pulse delay of 100 μsec; broadband proton decoupling was employed during acquisition. (Reference Hg(CH$_3$)$_2$ (external));

FIG. 7 is the $^1$H-Decoupled $^{195}$Pt NMR Spectrum of 5-(chloromercuri-1,2-pentane-diammine)dichloroplatinum(II) in NMP. Spectral Frequency=85.736 MHz; Recorded using a spectral window of 50 KHz, with a pulse width of 30 μsec, and a pulse delay of 100 μsec; total of 3200 scans collected; broadband proton decoupling was employed during acquisition; chemical shifts are reported relative to $K_2PtCl_6$=0 ppm; referenced using external $K_2PtCl_4$ ($\delta K_2PtCl_4$=−1623 ppm).

FIGS. 8–11: In vitro assay for crosslinking of proteins to DNA by 5-Chloromercuri-1,2-pentanediamine)dichloro platinum(II). Lane 1:4.5 pM DNA, 500 cpm Lane 2: DNA+ 460 pM MerR dimer Lane 3: DNA+protein+2.4 nM unlabeled competitor DNA Lane 4: DNA+protein+25 mM KCN Lane 5:DNA-protein complex treated with 10 mM 1 prior to competition. Lane 6: DNA-protein complex treated with 2 mM 1 prior to competition. Lane 7: DNA-protein complex treated with 0.4 mM crosslinker prior to competition Lanes 8–10: Reactions as for lane 5–7, pretreated with 25 mM KCN prior to competition. (Grant)

Figure 8:
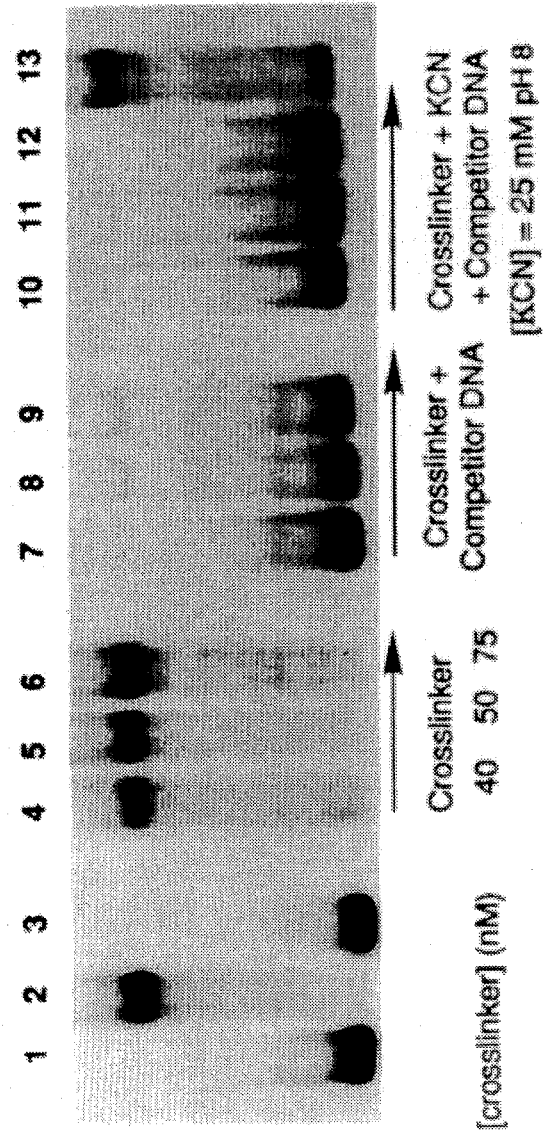

FIG. 8 illustrates the results of a cross-linking assay for the MerR protein.

Figure 9:
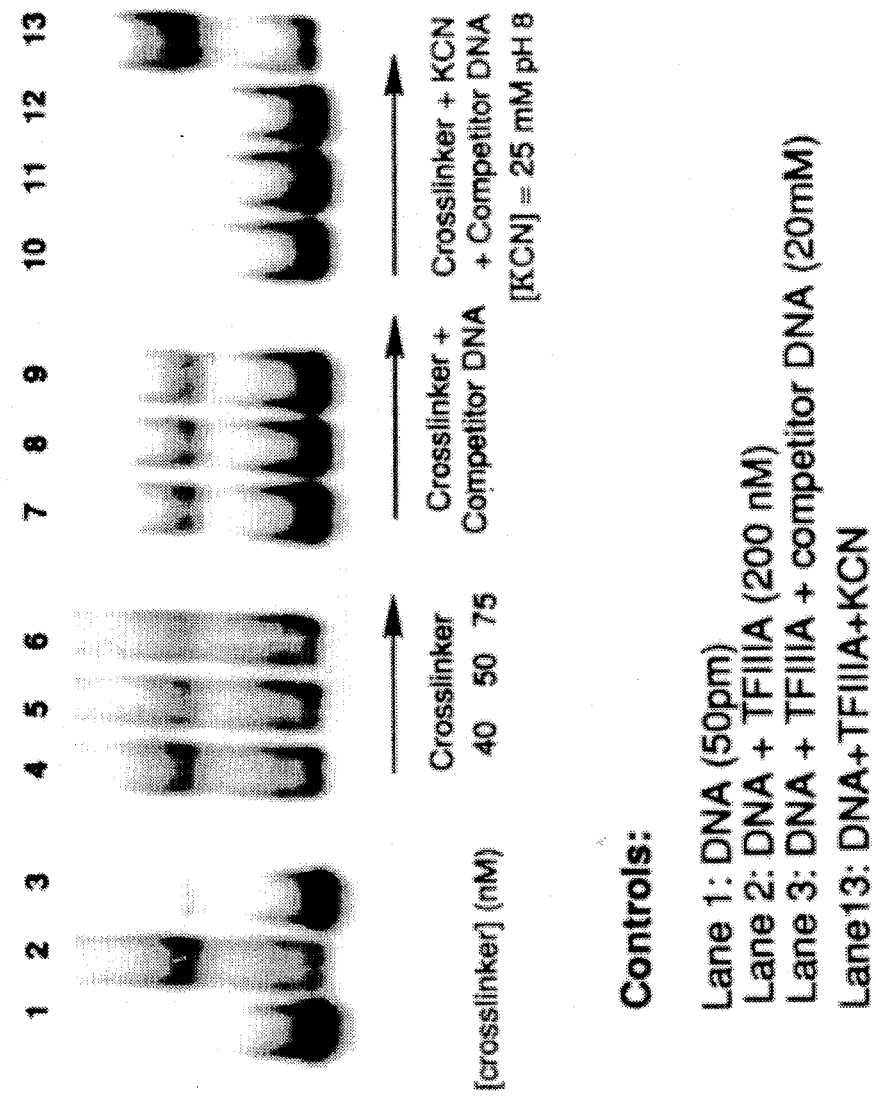

FIG. 9 illustrates the results of a cross-linking assay for the TFIIIA protein.

Figure 10:
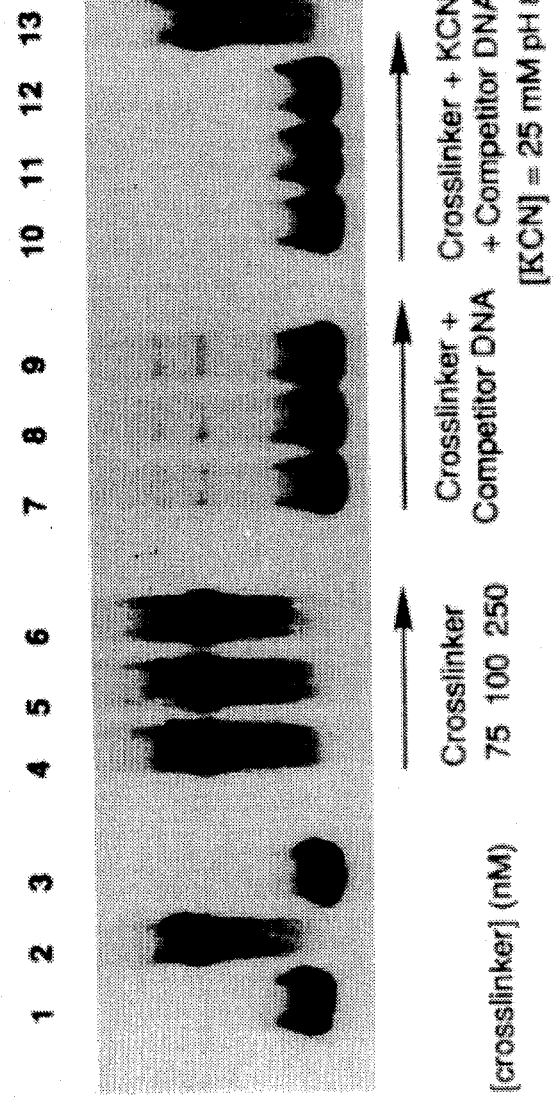

FIG. 10 illustrates the results of a cross-linking assay for the Fur protein.

Figure 11:
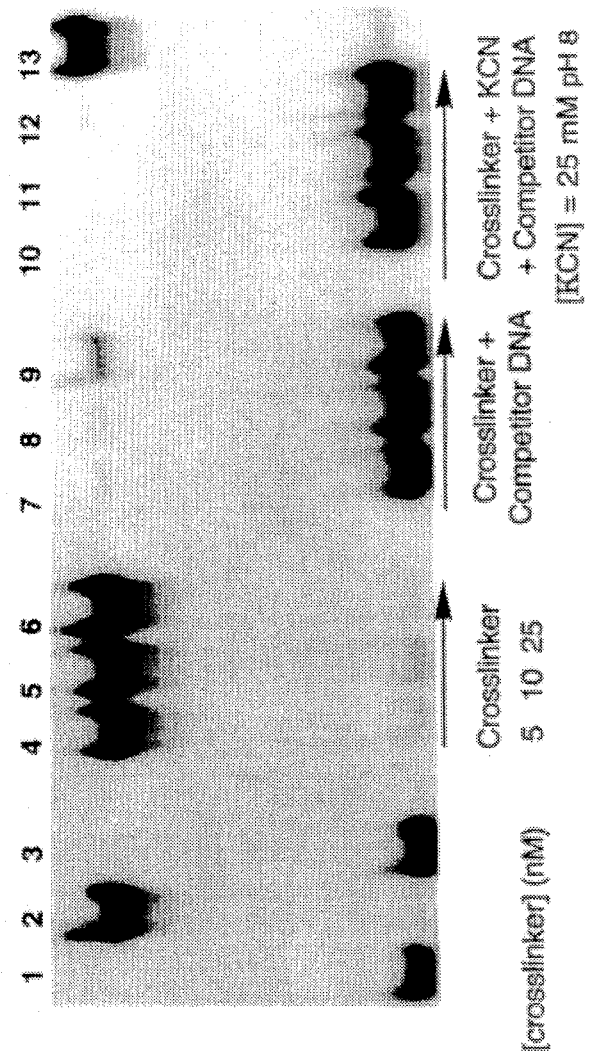

FIG. 11 illustrates the results of a cross-linking assay for the GAL4 protein.

Figure 12:
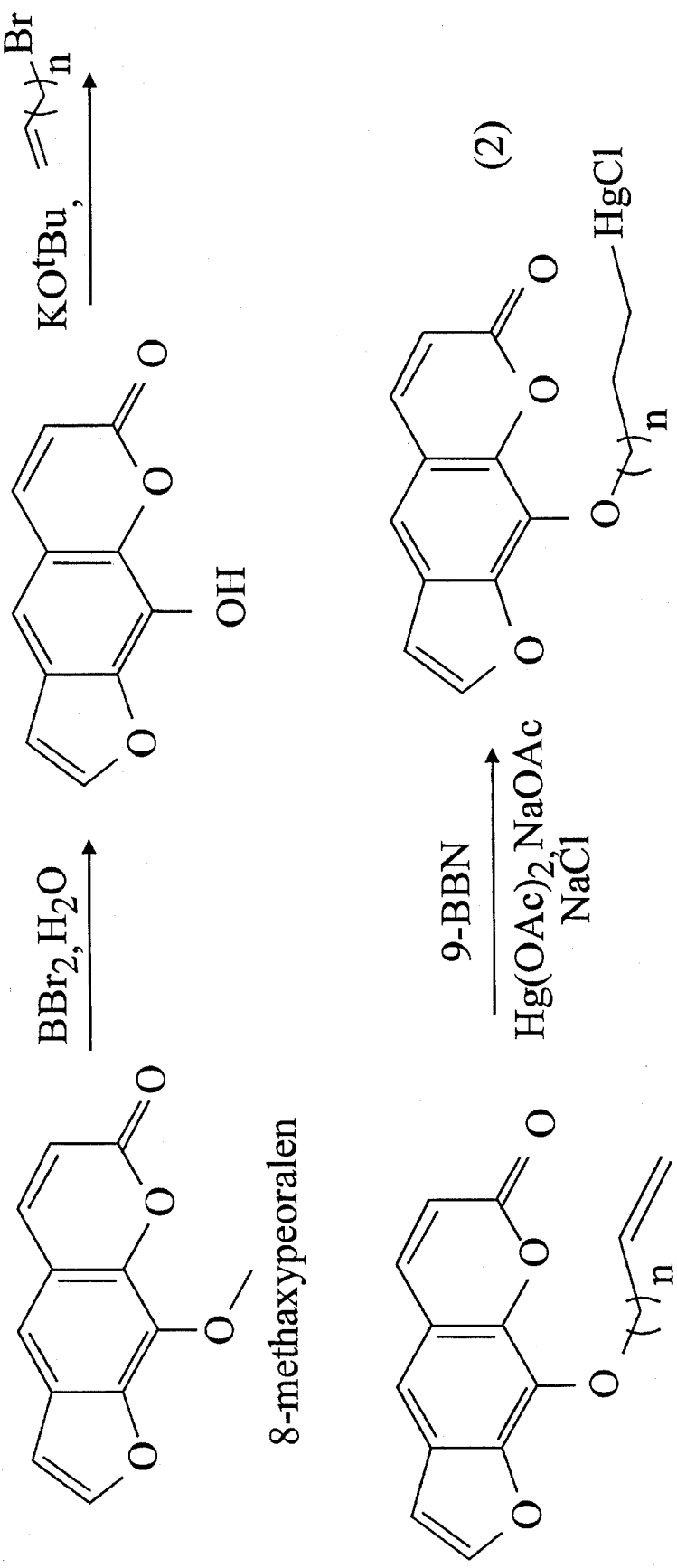

FIG. 12 is a schematic representation of the synthetic scheme for the preparation of a psoralen-based analog to the crosslinking reagents of the present invention.

Figure 13:
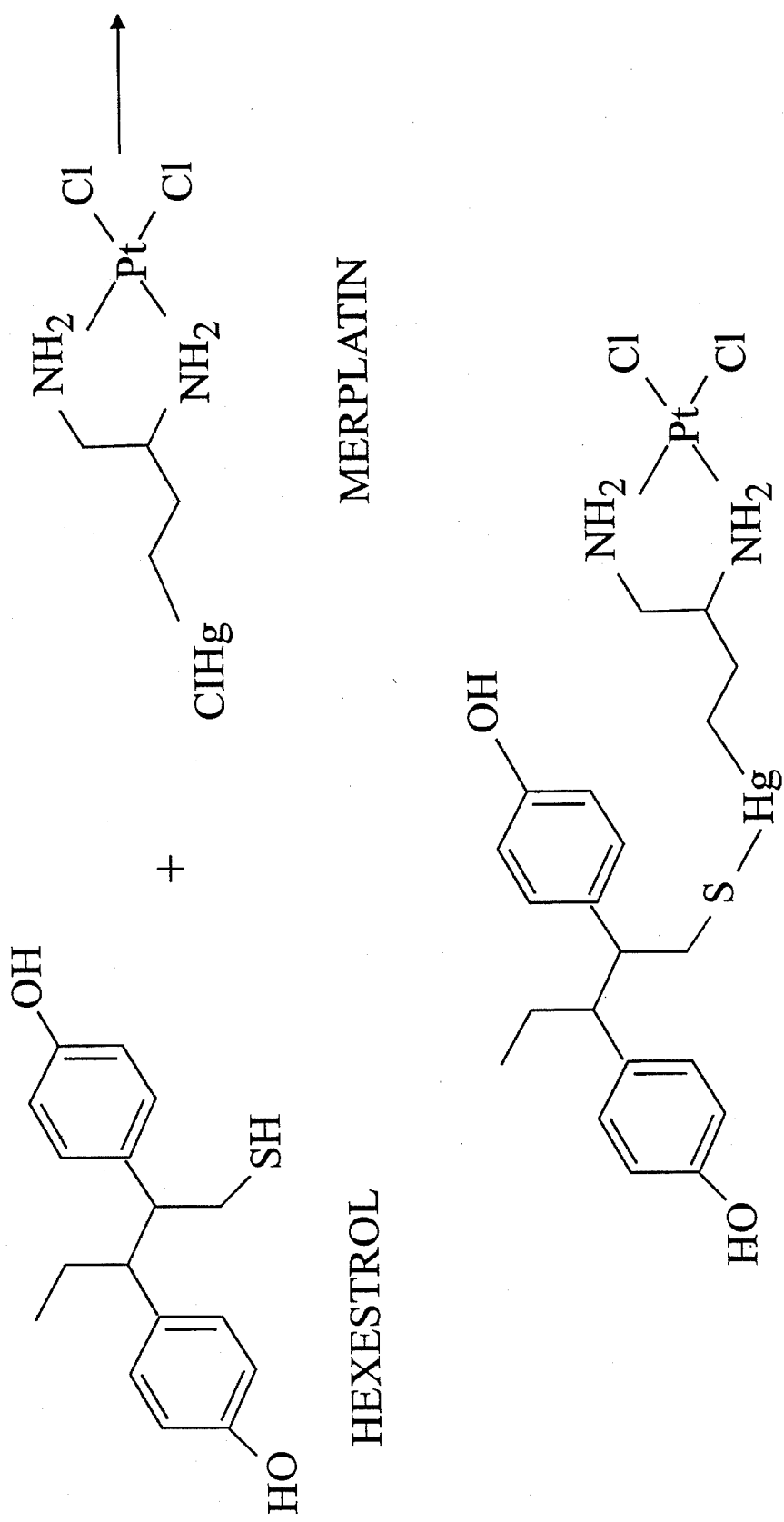

FIG. 13 is a representation of the reaction between the non-steroidal estrogen hexestrol and 5-Chloromercuri-1,2-pentanediamine)dichloro platinum(II).

DETAILED DESCRIPTION OF THE INVENTION

Disclosed herein is a novel class of bimetallic cross-linking reagents, referred to collectively as the Merplatins, that take advantage of distinct biological reactivities of two different metal species to afford the maximum possible specificity to these reagents in reactions linking DNA and protein molecules. Exemplary of these complexes is the species shown in FIG. 1, composed of a DNA-binding cis-diaminedichloroplatinum(II) complex (cis-DDP or cisplatin) (Sherman & Lippard, 1987), tethered via a flexible aliphatic linker chain to an organomercurial species, which performs the protein-binding function of the reagent (Falchuck et al., 1977). The flexibility of the linker chain aids the reagent in formation of crosslinks, since it will accommodate a variety of distances and geometries between the ligands presented by DNA-protein complexes.

In one embodiment, the present invention contemplates a bi-metallic cross-linking reagent according to the formula below:

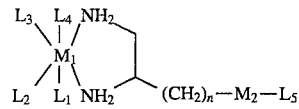

wherein $M_1$ is a metal ion species capable of forming a complex of coordination number four or coordination number six; wherein $L_1$, $L_2$, $L_3$, and $L_4$ are each independently a halide, ammonia, dimethyl sulfoxide, carboxylate, thiolate, imidazole, a nucleobase, or an empty coordination site, provided that no more than two of $L_1$, $L_2$, $L_3$, and $L_4$ are empty coordination sites; wherein $M_2$ is a metal ion species capable of forming a complex of coordination number two with a first ligand that is a hydrocarbon moiety and a second ligand that is kinetically labile; and wherein n is an integer from two to nine.

Preferably, the present invention contemplates a cross-linking reagent wherein $M_1$ is platinum, ruthenium, palladium or nickel. More preferably, the present invention contemplates a cross-linking reagent wherein up to three of $L_1$, $L_2$, $L_3$, $L_4$ and $L_5$ are each a halide, or, more preferably still, where the halide is chloride. Alternatively, the present invention contemplates a cross-linking reagent wherein $M_1$ is platinum(II), and up to two of $L_1$, $L_2$, $L_3$ and $L_4$ are empty coordination sites. More preferably, $M_1$ is platinum(IV), and none of $L_1$, $L_2$, $L_3$ and $L_4$ are empty coordination sites. Even more preferably, the present invention contemplates a cross-linking reagent wherein $M_2$ is mercury(II), and n is an integer from three to five. Alternatively, n is three or five.

Also disclosed herein is the design and synthesis of a novel class of bimetallic crosslinking agents which combine the different biological reactivities of two transition metal complexes in a single bifunctional reagent. Design of the cross-linking reagents is based on the known high affinity of platinum antitumor agents such as cis-diamminedichloroplatinum(II) for nucleic acids (Sherman & Lippard, 1987), and the high affinity of organomercurial species for soft residues in proteins, such as —SH (cys), —SCH$_3$ (met) and imidazole (his) (Wright et al, 1990; Falchukj et al., 1977). By coupling the reactivities of these two metal ions into a single molecule, a higher degree of efficiency to the crosslinking reaction is achieved than is demonstrated by the simpler reagents such as cis- and trans-DDP, which can also mediate a large degree of protein-protein crosslinking.

In another aspect, the present invention embodies a bi-metallic nucleotide/peptide cross-linking reagent according to the following formula:

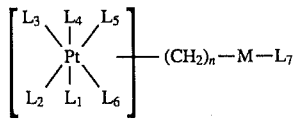

wherein $L_1$ to $L_6$ are each independently amine, a halide, cyclohexylamine, carboxylato, or empty coordination sites, provided that no more than two of $L_1$–$L_4$ are empty coordination sites; wherein any two of $L_1$ to $L_6$ are together cyclobutane-1,1-dicarboxylato-O,O', tetrahydro-4H-pyran-4, 4-dimethanamine-N,N', 1,2-diaminecyclohexane-N,N', or 2,2-bis(aminomethyl)- 1,3propanediol; wherein M is a metal ion species capable of forming a complex of coordination number two with a first ligand that is a hydrocarbon moiety and a second ligand that is kinetically lablie; wherein L7 is a ligand that forms a kinetically lablie coordination bond with M; and wherein n is an integer from 2 to 9. Preferably, the present invention embodies a cross-linking reagent of where M is mercury(II) and n is an integer from three to five.

Figure 3:
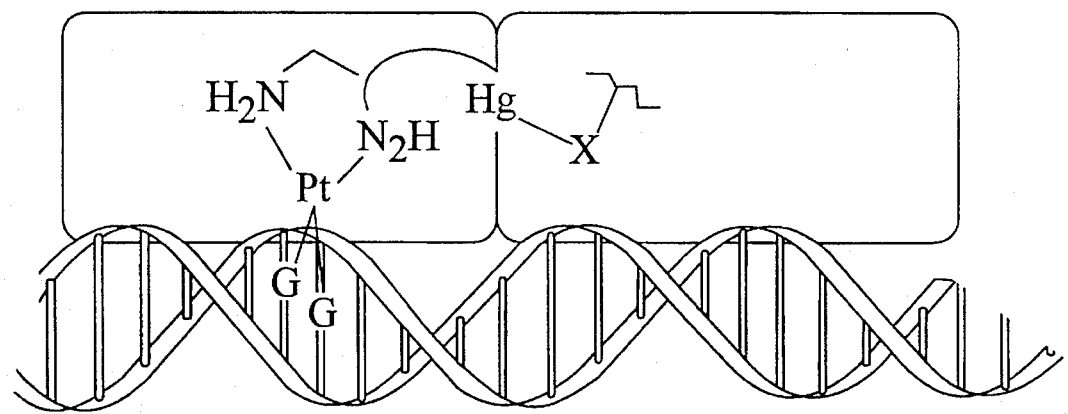
FIG. 3 is a schematic representation of the mode of reversible protein-DNA crosslinking mediated by bimetallic reagents.
Figure 3:
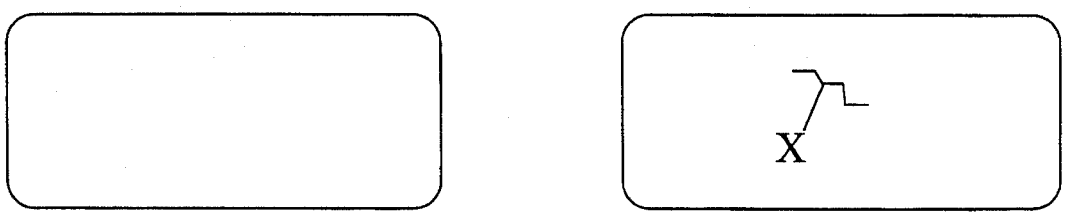
Figure 3:
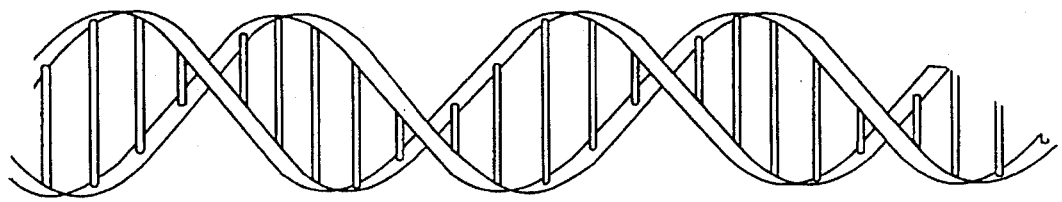
Figure 3:
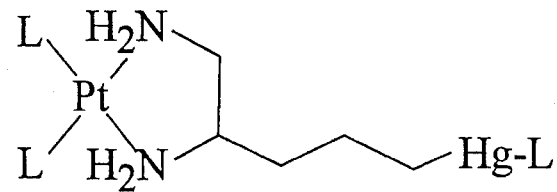

As shown schematically in FIG. 3, the reagent mediates the formation of strong covalent adducts between DNA and bound protein molecules. These cross-links can be reversed by competition with an excess of a ligand with a high affinity for the metal ions, such as a thiol, thiourea, or cyanide, without residual modification of the protein or DNA (Ciccarelli et al., 1985; Miller & Costa, 1989).

In an alternative embodiment, the present invention encompasses a method for reversibly linking a first molecule to a second molecule, comprising the steps of (a) reacting the first molecule with the bi-metallic cross-linking reagent pictured above under conditions effective to bind a first metal ion center of the bi-metallic reagent to the molecule; and (b) reacting the product of part (a) with the second molecule under conditions effective to bind a second metal ion center of the bi-metallic reagent to the molecule. Preferably, the present invention embodies a method where the first molecule reacted is a polynucleotide and the second molecule is a protein, a peptide, or a molecule comprising a thiol moiety. However, the order of reacting the first and second molecules is immaterial to the practice of the method of the present invention and the designations of "first" and "second" molecule are for convenience in reference only. More preferably, the protein utilized in the method of the invention is a metalloregulatory protein or a protein that comprises a zinc-finger motif. More preferably still, the protein is MerR, Fur, GAL4, or TFIIIA. Alternatively, the molecule comprising a thiol moiety is a thioether, a phosphothiolate or, by way of example, hexestrol.

The widely different ligand substitution rates exhibited by the two metal ions in the cross-linker is expected to enhance the specificity of the species toward formation of DNA-protein cross-links. Since reactions at Hg(II) occur with essentially diffusion-controlled kinetics (Rabenstein & Reid, 1984), the organomercurial entity exchanges rapidly between low-molecular weight thiol-containing compounds such as glutathione, and exposed sulfur- and nitrogen-containing residues in proteins. This rapid exchange facilitates the transport of the reagent within the cell, allowing it to pass between binding sites of comparable thermodynamic stability. This interchange will continue until the much slower reaction of the platinum moiety (Bancroft et al., 1990) results in binding of the reagent to DNA (or other cellular targets).

At this point, the mercurial is effectively anchored in place by the thermodynamic and kinetic stability of the platinum-DNA binding; as a consequence it is disposed to react with ligands derived from proteins bound in the vicinity, forming the desired DNA-protein cross-links. The binding energy associated with specific DNA-protein interactions contributes to the overall stability of the crosslinking interaction, in essence providing stabilization of specific cross-links via a "macrochelate" or multidentate effect.

In yet another embodiment, the present invention discloses a linked species where a first molecule is linked to a second molecule through the bi-metallic cross-linking reagent described above, wherein the linked species is preparable by the process of (a) reacting the first molecule with the bi-metallic cross-linking reagent of claim 1 under conditions effective to bind a first metal ion center of the bi-metallic reagent to the molecule; and (b) reacting the product of part (a) with the second molecule under conditions effective to bind a second metal ion center of the bi-metallic reagent to the molecule. Preferably, the present invention discloses a linked species where a first molecule is linked to a second molecule through the bi-metallic cross-linking reagent wherein the linked species is actually prepared by the process of (a) reacting the first molecule with the bi-metallic cross-linking reagent under conditions effective to bind a first metal ion center of the bi-metallic reagent to the molecule; and (b) reacting the product of part (a) with the second molecule under conditions effective to bind a second metal ion center of the bi-metallic reagent to the molecule. More preferably, in the linked species used in the method of the present invention $M_1$ is platinum(II), $M_2$ is mercury(II), $L_2$, $L_3$, and $L_5$ are each chloride, and n is three or five. Also, the method of the present invention utilizes a second molecule that is a polynucleotide. Preferably, the first molecule is a protein, a peptide, or a molecule comprising a thiol moiety. More preferably, the protein is MerR, Fur, GAL4, or TFIIIA.

As discussed above, the platinum entity of the cross-lining reagent of the present invention, cis-dicholorodiammineplatinum(II) (cisplatin), is one of the most widely used anticancer drugs. This compound has been attributed a curative and head and neck carcinomas. Activity against breast cancer has been noted in some cases. Unfortunately, many tumors exhibit resistance to the drug even after a short course of treatment. While second generation drugs such as carboplatin have been proven to be less toxic in clinical trials, most evidence indicates that cisplatin-resistant carcinomas are also resistant to carboplatin treatment.

In still another embodiment, the present invention contemplates a linked species comprising a cell-specific molecule and the bi-metallic cross-linking reagent described above. Preferably, the present invention contemplates a linked species where a first metal center of the bi-metallic cross-linking reagent is linked to the cell-specific molecule and a second metal center of the cross-linking reagent comprises an anti-tumor agent. More preferably, the anti-tumor agent is selected from the group consisting of cisplatin, carboplatin, JM-216, tetraplatin, zeriplatin, and enloplatin, and the cell-specific molecule is a cell surface receptor or a nuclear receptor.

The Merplatin reagents of the present invention incorporate novel features not found in available cross-linking or anti-tumor agents: a protein-DNA crosslinking function and a site for linkage of biological ligands for targeted delivery. The binding functions of each metal-based entity within the Merplatins have been retained unaltered through covalently tethering the organomercurial moiety to the amine groups of the cisplatin moiety in a manner that does not disrupt the DNA binding activity of the platinum center. The results of biochemical assays on a number of DNA-binding proteins, including, among others, the eukaryotic transcription factor TFIIIA, indicate that the organomercurial adds an efficient protein crosslinking activity which cannot be attained by cisplatin alone. Covalent crosslinking of proteins in vivo to platinum-modified cites on DNA will likely make the Pt-DNA lesions less susceptible to repair processes and thus more cytotoxic. Accordingly a novel spectrum of biological activity is possible with the Merplatin reagents of the present invention.

In still another embodiment, the present invention contemplates a method of delivering an anti-tumor agent to a cell where a specific cell type is targeted for delivery of the agent, the method comprising the step of administering the linked species described immediately above.

Using the cross-linking reagent of the present invention, it is possible to elevate the concentration of cisplatin (as part of the cross-linking reagent) in specific cell types through a receptor-mediated process. To accomplish this, a variety of estrogen analogues, such as hexestrol, are covalently coupled to a merplatin reagent. Subsequently, the cell-specific interactions of these estrogen analogs, covalently tethered to the anti-tumor moiety, in estrogen-receptor positive breast cancer cell lines can effectively target the cytotoxic agent to the cells of interest.

Cisplatin is known to have a high affinity for N7 positions of guanine, favoring the formation of intrastrand G-G cross-links on double helical DNA. (See FIG. 3.) Organomercurial species favor binding to polarizable atoms in protein side change such as the —RSH group of cysteine or the —RSCH$_3$ group of methionine. However, the molecular binding activity of metal complexes such as the organomercurial species disclosed as part of the cross-linking reagent of the present invention is not limited solely to protein molecules. As would be recognized by one of skill in the appropriate chemical arts, any molecular species possessing a thiol moiety, including thioethers and phosphothiolates, would be capable of binding to the organomercurial species of the present invention, as well as to other metal ion complexes with the appropriate characteristics. Of importance here, in the context of applications involving reversible cross-linking, the kinetic and thermodynamic properties of such binding would be critical. However, in those applications where the thermodynamic and kinetic characteristics of the complex resulting from the metal-thiol binding are less specific, a wider array of metal and organic species would be appropriate candidates for forming a bound entity.

Protein and DNA-binding assays reported infra indicate that the Merplatin reagents of the present invention retain the binding characteristics of both the unlinked cisplatin moiety and the unlinked organomercurial, Furthermore, while both cisplatin and Merplatin bind avidly to DNA, only the latter reagent can efficiently induce DNA-protein cross-links between a variety of proteins such as Fur, MerR, and the zinc finger transcription factor TFIIIA, and the DNA fragments bearing the respective recognition sequences.

Thus Merplatin reagents can be tethered to a variety of biological ligands and used to probe the effects of the resulting adducts in receptor-positive cell lines. The merplatins can be readily conjugated to drugs and hormones through a simple chemical reaction at the organomercurial portion of the molecule, as described in detail above. This novel property of the merplatins allows the attachment of a biologically active platinum anticancer moiety to natural or engineered cysteine-containing peptides, proteins, enzymes, antibodies, carbohydrates or to any drug that has a thiol moiety. A tightly bound covalent adduct is formed in a rapid reaction that is capable of being carried out by clinical personnel at bed-side. The adduct is formed at room temperature upon mixing a solution containing a Merplatin with a solution containing the target drug or peptide.

While the present invention contemplates a variety of peptide adducts including human growth hormone with the bi-metallice cross-linking reagent described herein, only a steroid-receptor scenario is discussed in detail below, by way of example. It is important to note that Merplatin adducts with ligands that have specific extracellular receptors such as transferrin, could be employed using the strategies outlined here. Since Merplatin is stable at low pH a variety of endocytic pathways can be targeted.

A candidate species contemplated in the practice of the present invention is a thiol derivative of the non-steroidal estrogen hexestrol. (Katzenellenbogen, personal communication.) The presence of a thiol entity on the hexestrol molecule (see FIG. 13) makes it possible to prepare a variety of conjugates, including those with the cross-linking reagents of the present invention, for which estrogen receptor binding affinity has been demonstrated. The reaction of hexestrol with a Merplatin reagent of the present invention is presented in FIG. 13.

Key to the utility of the practice of the present invention is the fact that, for a cross-linked species such as that shown as the reaction product of the scheme presented in FIG. 13, although thiol groups can bind tightly to he organomercurial portion of the crosslinking reagent, one thiol can readily replace another in a rapid reaction. As recognized, facile thiol exchange reactions are typical of organomercurials. Upon diffusion of a Merplatin cross-linked hexestrol species into a target cell, the organomercurial portion of the conjugate would be exposed to elevated concentrations of low molecular weight intracellular thiols. Depending on the concentration of these thiols and the rate of hexestrol complexation to the estrogen receptor, the platinum moiety of the cross-linker could be released from the hexestrol after entering the nucleus, providing effective delivery of the cytotoxic platinum species to DNA of the cell. It is also possible to exert control over the thiol exchange rate of the linked species through synthetic schemes which introduce sterically bulky moieties at the mercurial-linked methylene carbon of the thiol molecule. This control of substitution kinetics will make it possible to insure that release of the platinum moiety does not occur until after the linked species enters the nucleus of the cell, thus insuring maximum cytotoxic effect.

EXAMPLES

The following examples illustrate particular embodiments of the present invention and are not limiting of the specification and claims in any way.

EXAMPLE 1

Preparation of Merplatin Cross-linker Species

All reagents were purchased from Aldrich Chemical Co., Milwaukee, Wis., except where otherwise noted, and used as supplied. Allyl bromide was distilled prior to use to remove a brown impurity. Solvents were from Malinckrodt, and were used as received, with the exception of tetrahydrofuran, which was freshly distilled from sodium benzophenone ketyl immediately prior to use. Diphenyl ketimine was prepared according to the published Procedure, or was purchased from Aldrich. Deuterated solvents were obtained either from Aldrich Chemical Co., or from Isotech. Elemental analyses were performed by Midwest Microlabs, Inc, Cleveland, Ohio.

Platinum and mercury analyses were performed using an AtomScan-25 Inductively Coupled Plasma (ICP) Atomic Absorption Spectrometer (AA). Pt and Hg emission intensities were measured at 214.42 nm and 194.23 nm, respectively. Metal standard solutions (1020 µg/ml in 1% $HNO_3$) were used as obtained from Aldrich. The instrument was calibrated using deionized water and the standard solutions as low and high standards, respectively. 0.1N $HNO_3$ was run through the inlet tubing until a zero reading was obtained, after standardization and between sample readings.

Preparation of the Ligand Framework

The procedure outlined below for the preparation of the ligand framework upon which the cross-linker is based was designed to incorporate a route which could be simply modified to permit synthesis of crosslinkers with varying spacer lengths between the metal ions. The protocol below was therefore developed to be amenable to the attachment of a variety of side-chains onto the ethylenediamine moiety.

The overall approach is based upon a phase-transfer alkylation procedure developed by O'Donnell and coworkers (O'Donnell & Eckrich, 1978; O'Donnell et al., 1989). In this method, a diphenyl ketimine acts both to protect the amino group and to activate the α-carbon of the molecule towards deprotonation. The alkylation can be carried out conveniently under very mild conditions ($CH_2Cl_2$/50% NaOH), and gives excellent yields of the monoalkylated product. Most importantly, the method accommodates a wide variety of alkylating agents, allowing simple modification of the preparative scheme to effect the preparation of ligands with a variety of alkyl chain lengths. The procedure may also be modified to generate enantiomerically enriched compounds by using a chiral phase transfer agent in the alkylation.

Step 1 2-(Diphenylmethylimino)-acetonitrile.

The iminoacetonitrile was prepared according to published literature procedures (O'Donnell & Polt, 1982).

Step 2 2-(Diphenylmethylimino)-4-pentenenitrile.

A 9.4-g sample (42.6 mmol) of the compound prepared in step 1 (2-(Diphenylmethylimino)-acetonitrile) was dissolved in 50 mL of dichloromethane, and the solution was cooled in an icebath. Benzyltriethylammonium chloride (1.05 g, 4.26 mmol) and NaOH (50% aq, 10.3 g) were added, upon which the solution developed a brown color. The mixture was stirred vigorously as allyl bromide (6 mL, 8.40 g, 70.0 mmol) was added slowly over the course of 1 hour, and the brown color slowly faded to a light orange. The mixture was stirred for 1 hour and allowed to warm to room temperature. At this point, the alkylation was complete as evidenced by TLC analysis on silica gel, with 2.5% ethyl acetate/hexanes as the mobile phase.

The mixture was then poured into a separatory funnel containing 100 mL of dichloromethane and 100 mL of $H_2O$. The layers were separated, and the aqueous layer was extracted with three 50-mL portions of dichloromethane. The combined extracts were washed with two 50-mL portions of $H_2O$ and a single 50-mL portion of saturated NaCl; dried over $MgSO_4$; and evaporated to give a light brown oil. This oil was distilled using a Kügelrohr apparatus to give a slightly yellow tinted oil (b.p. 105°–110° C. at 0.5 mmHg). The procedure produced a yield of 9.94 g of the product, which translated to a 90% yield.

[characterization of product: $^1H$ NMR ($CDCl_3$): δ 2.56–2.65(m, 1H), 2.67–2.75(m, 1H), 4.28(t, 1H), 5.19(m, 2H), 5.80(m, 1H), 7.19–7.66(m, IOH): $^{13}C$ NMR ($CDCl_3$): δ30.7, 52.6, 118.6, 119.1, 127.0, 127.8, 128.6, 129.0, 130.8, 131.6, 134.7, 138.0, 172.5. IR(liq. film): 2740(m), 2260(w), 1620(s), MS m/e (rel. intensity): 260(32) ($M^+$), 219(42) (M-allyl.), 182(32) (M-PhH), 116(100).]

Step 3 2-Amino-4-pentenenitrile hydrochloride.

Removal of the benzophenone imine is readily accomplished by treatment with dilute HCl, to afford the substituted aminonitrile hydrochloride in high yield. A 9.0 g sample (35 mmol) of the product of Step 2 (2-(Diphenylmethylimino)-4-pentenenitrile) was dissolved in pentane and stirred vigorously with 2N HCl (50 mL, 100 mmol). After about 2 hours, TLC analysis of the pentane layer (silica gel, 2.5% ethyl acetate/hexanes) revealed complete conversion of the diphenyl ketimine to benzophenone. The layers were then separated, the aqueous layer was washed with two 50-mL portions of pentane, and evaporated to dryness. The off-white solid was collected, and washed with ether. Recrystallization from methanol/ether gave the product as a white solid.

Despite the acidic nature of the hydrochloride salt, it is most convenient to use this compound directly in the reduction step, rather than to protect the amino group prior to reduction. The reduction proceeds efficiently, and appears to be complete in a matter of minutes at room temperature. Isolation of the diamine is hampered by the apparent formation of a strong chelate to the aluminum side-products, so that a simple extractive workup is not effective. Instead, it is necessary to isolate the diamine by treatment of the product mixture with concentrated alkali, and distillation of the aqueous azeotrope. Acidification and solvent removal gives the product as the hydrochloride salt in reasonable yield (4.44 g, 97%). Some difficulties with scale-up for this reaction have been encountered and, as a consequence, it is this step which currently limits the overall scale on which the crosslinker can be made.

[characterization of product: $^1$H NMR (D$_2$O): δ 2.6–2.82(m, 2H), 4.53(t, 1H), 5.40(m, 2H), 5.85(m, 1H). $^{13}$C NMR (D$_2$O): 38.43, 44.89, 119.58, 126.60, 132.77 IR (KBr disk): 3300–2200 (br. s), 2060(m), 1490(s), 940(s). MS m/e (rel. intensity): 96(4.7) (M-HCl), 70(5.4) (M-CN), 55(100).]

Step 4 4,5-Diamino-1-pentene dihydrochloride.

A 4.0 g sample (30.0 mmol) of the product of Step 3 (2-amino-4-pentenenitrile hydrochloride) was suspended in anhydrous ether (30 mL) in a N$_2$-flushed 3-necked flask equipped with a water-cooled condenser. Lithium aluminum hydride (1M in TBT, 33 mL/33 mmol) was added drop-wise via syringe, at a rate sufficient to maintain a gentle reflux. When the addition was complete, the white suspension was stirred an additional 30 minutes. The reaction was worked up by careful addition of 5 mL of a saturated Na$_2$SO$_4$ solution, followed by 10 mL of 50% NaOH, and 40 mL of H$_2$O. The flask was then equipped for distillation, and distilled until almost dry. The combined ether and aqueous distillates were acidified carefully with concentrated HCl, and the solvents were removed. The product was recrystallized from methanol/ether to afford a white microcrystalline solid, with a yield of 3.37 g (65%).

[Analysis calculated for C$_5$H$_{14}$N$_2$Cl$_2$: C 34.68%, H 8.15%, N 16.18%; found: C 34.8%, H 7.98%, N 15.50%; characterization: $^1$H NMR (D$_2$O): δ 2.50(m, 1H), 2.63(m, 1H), 3.35(dd, 2H), 3.72(m, 1H), 3.72(m, 11H), 5.32(s, 1H), 5.8(m, 1H); $^{13}$C NMR (D$_2$O): 5 36.96, 43.17, 51.26, 124.4, 132.83; IR (KBr disk): 3135 (br,s), 2809 (m), 1400 (s).]

Incorporation of the Metal Ions

Because of the possibility of adverse side-reactions of platinum(II) with the alkene functional group of the precursor diamine, it was decided to introduce the mercury species before the platinum. The amino groups are therefore blocked as the t-butoxycarbamate derivative, to prevent formation of Lewis acid-base complexes with the borane reducing agent. Incorporation of the organomercurial functionality is then readily accomplished by treatment with BH$_3$.THF to afford an organoborane intermediate, which is treated directly with mercuric acetate to generate the organometallic species. The complexes are isolated as the chloromercuri-derivatives, because these are more readily handled than the acetate derivatives initially formed in the reaction. Removal of the protecting groups with HCl in CH$_2$Cl$_2$ cleanly generates the diaminomercurial species, which is most conveniently isolated as the sulfate salt, due to the hygroscopic nature of the dihydrochloride.

The platinum is incorporated into the cross-linker species by a straightforward and mild reaction with Pt(DMSO)$_2$Cl$_2$,[32] to afford the geometric isomers cleanly and in good yield. Conversion to the chloride complex is accomplished simply by warming in HCl solution, upon which the neutral product is precipitated from solution as a yellow solid.

Step 5 1.2-di-(N-t-butoxycarbonylamino)-4-pentene.

A 3.0 g sample (17.3 mmol) of the product of Step 4 (1,2-diamino-4-pentene dihydrochlodide) was suspended in 25 mL of a 50:50 dichloromethane/ether mixture, and triethylamine (2.2 g, 22 mmol) was added. Di-tert-butyl-dicarbonate (4.80 g, 22 mmol) was then added, and the mixture stirred until gas evolution ceased. The mixture was washed with two 50-mL portions of water, dried, and evaporated. The resulting white solid was passed over a pad of silica gel, washed with ether, which was then dried, and the solvent removed to give a white solid in a yield of 5.0 g (96%).

[Analysis calculated for C$_{15}$H$_{28}$N$_2$O$_4$: C 60.0%, H 9.4%, N, 9.33%; found: C 59.25%, H 9.58%, N 9.12%; characterization: $^1$H NMR (CDCl$_3$): δ 1.46 (s, 18H), 2.23 (t, 2H), 3.20 (m, 2H), 3.70 (m, 1H), 5.11 (m, 2H), 5.78 (m, 1H); $^{13}$C NMR (CDCl$_3$): δ 28.35, 37.22, 44.19, 50.84, 79.34, 85.20, 118.09, 133.82, 156.0, 156.2; IR 3320 (s, br); 3000–2850 (s); 1730–1650 (s).]

Step 6 1,2-di-(N-t-butoxycarbonylamino)-5-chloromercuripentane.

A 2.0 g sample (6.7 mmol) of the product of step 6 (1,2-di-(N-t-butoxycarbonylamino)-4-pentene) was dissolved in 10 mL of anhydrous THF, and cooled in an icebath under N$_2$. BH$_3$.THF solution (1M in THF, 5 ml, 5 mmol) was added carefully over the course of five minutes. The solution was allowed to stir for 20 minutes, then solid Hg(O$_2$CCH$_3$)2 was added slowly, to give a grey suspension. The suspension was stirred under N$_2$ for 1 hour, then poured into 250 mL of ice water. Ten milliliters of a 1.0M sodium chloride solution were added with stirring, and the resulting mixture was extracted with dichloromethane. Drying and evaporation of the combined dichloromethane layers gave essentially pure product, which was used without further purification. The reaction produced 2.85 g of the product at a 98% yield.

[Analysis calculated for C$_{15}$H$_{29}$N$_2$O$_4$HgCl: C 33.52%, H 5.44%, N 5.21%; found: C 35.45%, H 5.56%, N 5.35%; characterization: $^1$H NMR (CDCl$_3$): 1.45(s, 18H); 1.84 (br m, 2H); 2.05 (t, 2H); 3.16 (br m, 2H); 3.46 (br m, 1H); 4.70 (br, 1H); 4.86 (br, 1H); $^{199}$Hg NMR (dmf): δ-794.3 IR: 3380 (m, br); 3000–2940 (m); 1690 (s); 1530 (m); 1400 (m); 1340 (m); 1255 (m) 1170 (s).

Step 7 1,2-diamino-5-chloromercuripentane sulfate.

A 2.5 g sample (4.7 mmol) of the product of Step 6 (1,2-di-(N-t-butoxycarbonylamino)-5-chloromercuripentane was dissolved in 10 mL of dichloromethane and stirred while HCl gas was bubbled into the mixture. Ten milliliters of water was added to dissolve the precipitated white solid, and the dichloromethane was removed in vacuo. Twenty milliliters of ethanol was added to the aqueous solution, followed by concentrated sulfuric acid (1 mL), resulting in precipitation of the white solid product, which was collected, washed with ethanol (10 mL) and ether (20 mL), and dried in air, yielding 1.9 g of product (95% yield).

[Analysis calculated for C$_5$H$_{15}$N$_2$O4SClHg: C 13.8%, H 3.47%, N 6.44%; found: C 14.26%, H 3.33%, N 5.25%; characterization: $^1$H NMR (D$_2$O): 1.86 (br m, 4H); 1.99 (br t, 2H) [$^{199}$Hg satellites at $^2J_{Hg-H}$=220 IU]; 3.35 (d, 2H); 3.70 (m, 1 H). $^{13}$C NMR (D$_2$O): 25.57, 30.57, 36.19, 42.85, 51.00; $^{199}$Hg NMR (D$_2$O): δ-816.1; IR (KBr disk): 3300–2500 (br, s); 2200 (br, w); 1550–1450 (m); 1170–1130 (br, s); 640 (s) 320 (m).]

Step 8 5-(chloromercuri)-pentane-1,2-diammine(dimethylsulfoxide)-chloroplatinum(II) chloride.

A 0.50 g sample (1.15 mmol) of the product of Step 7 (1,2-diamino-5-chloromercuripentane sulfate) was dissolved in 5 mL of H$_2$O, and 0.6 mL of triethylamine was added. A 0.48 g sample (1.15 mmol) of bis-(dimethylsulfoxide)dichloroplatinum(II), prepared from K$_2$PtCl$_4$ (as obtained from the Johnson Matthey Co.) according to an accepted literature procedure (Romeo, 1977) was added, and the mixture was stirred until all of the platinum complex had dissolved. Thirty milliliters of ethanol was added, and the mixture was evaporated to a volume of about 5 mL. A further 30 mL of ethanol were added, and evaporation was repeated. The resulting white solid was collected, washed with ethanol and ether, and dried in vacuo, yielding 0.58 g of product, at 75% yield.

[Analysis calculated for $C_7H_{19}N_2Cl_3SPtHg$: C 12.64%, H 2.88%, N 4.21%; found: C 13.03%, H 2.91%, N 4.24%; characterization: IR 3700–3400 (br, vv); 3040 (m); 3020 (m), 2920 (m); 1400 (m); 1300 (m); 1155 (s); 1132(s); 1040 (s); 738 (mw); 690 (mw); 430 (m); 380 (m); 332 (m); $^1$H NMR ($D_2O$): δ 1.55–1.8 (m,4H); 1.89 (m, 2H) ($^{199}$Hg satellite observed at 2.17 ppm: $^2J_{Hg-H}$=ca. 224 Hz); 2.58 (m, 2H); 2.87 (m, 1H); 3.08 (br. m); 3.38 (s, 6H); $^{13}$C NMR ($D_2O$); 25.9, 26.1, 30.4, 36.1, 36.2, 44.2, 51.7, 51.8, 60.1, 60.3; $^{195}$Pt NMR ($D_2O$): δ-3244, -3246 (ref: $K_2PtCl_6$); $^{199}$Hg NMR ($D_2O$): δ-1006. FAB-MS (m/e): 645 (M+), 610 (M Cl), 567 (M-DMSO) (isotope distribution of M+ matches well with calculated distribution).]

Step 9 5-Chloromercuri-1,2-pentanediamine)dichloro platinum(II).

A 0.50 g sample (0.74 mmol) of the product of Step 8 (5-(chloromercuri)-pentane-1,2-diammine(dimethylsulfoxide chloroplatinum(II)) was dissolved in 20 mL of 0.5N HCl, and warmed overnight at 50° C. The yellow precipitate was collected, washed with water, ethanol, and ether, and dried in a desiccator. The reaction produced 0.4 g of the product at a calculated yield of 90%. (The limited solubility of the complex in most solvents is a hindrance to recrystallization, and concerns over the stability of the complex on standing or heating in DMF or NMP complicate the problem further. When deemed necessary, the complex is purified by dissolution in DMSO and immediate precipitation with ethanol or chloroform).

[Analysis calculated for $C_5H_{13}N_2Cl_3PtHg$: C 9.96%, H 2.17%, N 4.64% Pt 32.34%, Hg 33.21%; found: C 10.23%, H 2.12%, N 4.90%, Pt 32.0%, Hg 35.1%. characterization: $^1$H NMR (DMSO-$d_6$): δ 1.45–1.75 (br, m, 6H); 2.11 (br, m, 1H); 2.33 (br, m, 1H) 2.58 (br, 1H) (overlaps with DMSO-d5); 5.03 (br, t, 1H), 5.24 (br, 1H), 5.36 (br, 1H); 5.50 (br, 1H); $^{13}$C NMR $d_6$-(DMSO): 25–75, 30.73, 35.03, 52.24, 60–11; $^{195}$Pt NMR (NMP/$d_7$-dmf): δ-2290 (ref: $K_2PtCl_6$); $^{199}$Hg NMR (NMP/d7 3–998 (ref: $Hg(CH_3)_2$); IR 3600–3100 (br, s) 2940 (m) 1650 (m) 1560 (ms) 1460 (mw) 1200 (m) 780 (mw) 330 (mw). FAB-MS M+=602. (Poor spectrum) (Addition of DMSO to aid dissolution in matrix led to M+=645 (M+DMSO–Cl)]

EXAMPLE 2

Alternative Preparatory Schemes

The crosslinker species prepared as described above has the potential of being an extremely useful tool to facilitate the identification and isolation of DNA-binding proteins, particularly metalloregulatory proteins whose natural function is to act as receptors for metal ions. The limited solubility of the complex has the potential to become problematic, however, particularly if administration of large doses of the complex are required for in vivo applications. An alternative approach producing a species with improved aqueous solubilities involves the dimethylsulfoxide (DMSO) of Step 8, above. The DNA-binding (Sundquist et al., 1987) and antitumor (Farrell, 1983) activities of DMSO-bound platinum complexes have been observed.

As one of skill in the relevant art would recognize, further modifications are also possible which can incorporate a platinum complex having only one labile ligand on the platinum, such as 3-amino-1-chloromercuripropane hydrochloride. A reagent of this type will have improved solubility in aqueous media, and will not have the site selectivity for GpG steps in DNA exhibited by cisplatin and its analogs. For both the DMSO and triamine-complexes, the presence of a positive charge in the molecule could interfere with the passage of the complex across cell membranes, although recent studies have demonstrated the antitumor activity of cationic platinum complexes, indicating that these complexes are capable of penetrating cells (Hollis et al., 1989; Hollis, 1991).

Preparation of such a species is straightforward, involving substitution into trans-DDP with 3-amino-chloromercuripropane. Chain-length modifications to the reagent can also be readily accomplished, since a homologous series of aminoalkenes is accessible via modification of the commercially available bromoalkenes.

Preparation of 3-Amino-1-Chloromercuripropane Hydrochloride

Step 1 3-t-Butoxycarbonylamino-1-propene.

To a solution of 38.24 g of di-t-butyldicarbonate (175 mmol) and 17.7 g of triethylamine (175 mmol) in 100 mL of ether, was slowly added a solution of 10.0 g of allylamine (175 mmol) in 50 mL of ether. When the addition was complete and gas evolution had ceased, the solution was washed with three 100-mL portions of 0.5N hydrochloric acid and a 100-mL portion of distilled water, then dried over $MgSO_4$. Removal of the solvent gave the product as a colorless liquid which crystallized slowly on standing to give large colorless crystals, producing 26.15 g of the product at a calculated yield of 94.8%.

[Characterization: $^1$H NMR ($CDCl_3$): δ=1.48 (s, 9H), 3.76 (br, 2H), 4.60 (br, 1H), 5.08–5.22 (m, 2H), 5.75–5.9 (m, 1H); IR (thin film on KBr plate): 3347 (ms), 3080 (w), 2976 (ms), 2927 (m), 1696 (s), 1522 (ms), 1392 (w), 1368 (m), 1278 (m) 1250 (m), 1174 (m).

Step 2 3-t-Butoxycarbonylamino-1-chloromercuripropane.

A 5.0 g sample (30 mmol) of the product of Step 1 (3-t-butoxycarbonylamino-1-propene) was dissolved in 20 mL of dry tetrahydrofuran (THF) under an inert argon atmosphere. $BH_3 \cdot THF$ (1M in THF, 20 mL) was added carefully in discrete portions, allowing gas evolution to subside between aliquots. The solution was stirred for 30 minutes, then solid mercuric acetate ($Hg(OAC)_2$) was added, and the resulting grey suspension was stirred for 30 minutes. The mixture was then poured into 200 mL of ice-cold NaCl solution. The mixture was extracted with three fifty-milliliter portions of dichloromethane, the combined extracts were washed with three fifty-milliliter portion of water, dried, and evaporated to give a grey solid. This was taken up in 50 mL of dichloromethane, filtered to remove the small amount of grey powder remaining and evaporated to give the product as a white solid in the amount of 7.05 g, representing a 60% yield.

[characterization: $^1$H NMR (DMSO-$d_6$): δ=1.43 (1, 9H), 1.68 (t, 2H), 1.79 (m, 2H), 2.98 (m, 2 H), 6.88 (br t, 1H); $^{13}$C NMR (DMSO-$d_6$): δ=27.4, 42.3, 76.6, 135.3, 148.6, 154.8. IR (KBr pellet): 3650–3050 (br, w), 2972 (w), 2924 (w), 2864 (w), 1686 (s), 1526 (s), 1448 (mw), 1367 (m), 1276 (s), 1249 (s), 1169 (s), 1018 (w), 853 (w), 625 (mw).]

Step 3 3-Amino-1-Chloromercuripropane.

A 5.0 g sample (12.8 mmol) of the product of Step 2 (3-t-butoxycarbonylamino-1-chloromercuripropane was dissolved in 10 mL of ethanol, and an equal volume of concentrated HCl was added. After stirring for 15 minutes, gas evolution had ceased. Addition of a further 10 mL of ethanol and 40 mL of ether gave the product as a white microcrystalline solid which was collected, washed with ether and dried in air, yielding 3.87 g of product (92% yield).

[Analysis Calculated for $C_3H_9NClHg$: C 10.90%, H 2.74%, N 4.24%; found: C 11.06%, H 2.67%, N 4.36%; $^1H$ NMR ($D_2O$): δ 1.94 (t, 1H), 2.11 (m, 1H), 3.07 (t, 1H); the two upfield signals exhibit $^{199}Hg$ satellite peaks with $^2J_{Hg-H}$ of 112 Hz (1.94 ppm signal) and 125 Hz (2.11 ppm signal); IR (KBr pellet): 3300–2700 (br, mw), 1595 (ms), 1505 (s), 1387 (m), 1169 (s), 1114 (ms), 1003 (s), 937 (s), 694 (s).]

EXAMPLE 3

Characterization of Merplatin Cross-Linker Species

Instrumental Conditions $^1H$, $^{13}C$, $^{195}Pt$ and $^{199}Hg$ NMR spectra were recorded on a Varian VXR-400 Fourier Transform spectrometer, operating at 399.95 MHZ ($^1H$), 100–595 MHz ($^{13}C$), 85.736 MHz ($^{195}Pt$), and 71.600 MHz ($^{199}Hg$). Standard acquisition parameter files were used for the accumulation of $^1H$ and $^{13}C$ spectra. For $^{195}Pt$ NMR, a spectral window of 50 KHz was used, with a pulse width of 30 μsec, and a pulse delay of 100 μsec. Broadband proton decoupling was employed during acquisition of the spectra. $^{195}Pt$ spectra were referenced externally using a 0.1M aqueous solution of $K_2PtCl_4$ in 0.1M KCl. Chemical shifts are reported relative to $K_2PtCl_6$=0 ppm. ($δK_2PtCl_4$=1623 ppm). Proton-decoupled $^{199}Hg$ NMR spectra were recorded using a spectral window of 30 KHz, a pulse width of 30 μsec, and a pulse delay of 100 μsec. Chemical shifts are reported relative to external $Hg(CH_3)_2$ (0 ppm). Mass spectra were recorded using a VG instruments VG70-250 S/SE instrument. Infrared spectra were recorded using either a Perkin-Elmer PE-283 or a Mattson Alpha Centauri FTIR spectrometer. UV spectra were obtained using a Hewlett-Packard HP8452 spectrophotometer running off of an IBM-AT personal computer. Kinetic measurements were controlled using the Hewlett-Packard Multicell Kinetics Module. Data manipulation and plotting was performed using the program Igor[24] running on a Macintosh IIx personal computer. Melting points were obtained using a Fisher-Johns hot stage apparatus.

Results

The cross-linker species of the present invention has been characterized by a combination of analytical and spectroscopic techniques. The complex has low solubility in water and most organic solvents. Prepared as described in Example 1, it exhibits limited solubility in amide solvents such as dimethylformamide or 1-methylpyrrolidinone (NMP), permitting the preparation of ~10 mM solutions. The complex is quite soluble in DMSO, although a warning has been issued concerning the compositions of DMSO solutions of cisplatin derivatives (Sundquist, 1987). The proton NMR spectrum of the complex in d7-DMF is poorly resolved, and the resonances due to the residual protons in the deuterated solvent tend to obscure parts of the spectrum of the complex.

The $^1H$ NMR spectrum of a freshly prepared solution of 5-(chloromercuri-1,2-pentanediamine)dichloro platinum(II) in $d_6$-DMSO solution is shown in FIG. 4. The signals also exhibit a tendency to broaden in this solvent, but nevertheless, the presence of the ligand may be discerned quite readily. Precise assignment of the three peaks which appear in the 2.0–2.7 ppm region of the spectrum is difficult because of the poor quality of the coupling information, but they are thought to arise from the ethylene diamine portion of the ligand skeleton on the basis of chemical shift and relative intensities. The resonance at 2.58 ppm is assigned to the methine proton, since C-H protons tend to occur at higher field than methylenes. Exact integration of this peak is not possible due to overlap with the peak arising from residual protons in the solvent ($d_5$-DMSO).

An unexpectedly large difference in the chemical shifts of the resonances assigned to the diastereotopic methylene protons (see multiplet e of FIG. 4) is observed in this spectrum, but the relative integrations of these signals are clearly indicative of single proton resonances. Similarly, four well-separated resonances are observed for the N-H protons. A resonance at approximately 3.4 ppm cannot be assigned to the complex. Examination of the spectrum of the solvent revealed that a substantial portion of the resonance arises from this source, but it cannot be stated unequivocally that none of the signal observed in this region arises from the sample. However, no resonance corresponding to this impurity is detected in the $^{13}C$ spectrum of a more concentrated sample of the cross-linker complex in the same solvent, and it is concluded that the contaminant, if it arises from the sample at all, constitutes an extremely minor component.

Figure 1:
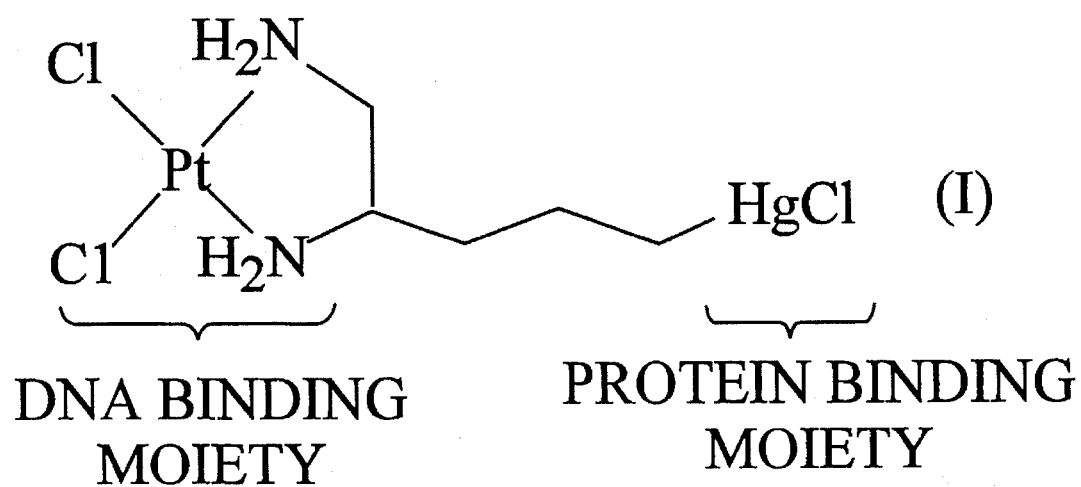
FIG. 1 is a representation of the structure of a representative Merplatin cross-linking reagent, 5-Chloromercuri-1,2-pentanediamine)dichloro platinum(II).
Figure 2:
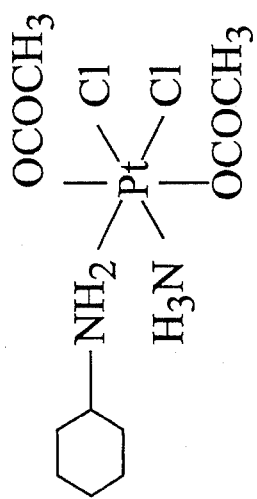
FIG. 2 is a representation of the structural formulas of cisplatin and related platinum analogs.
Figure 2:
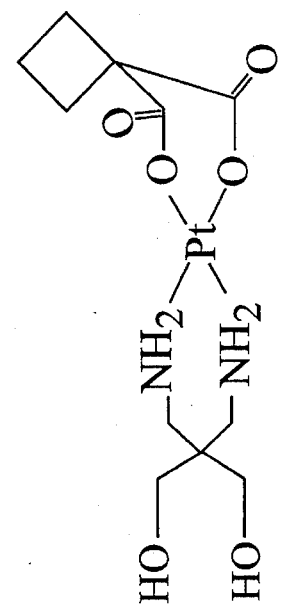
Figure 2:
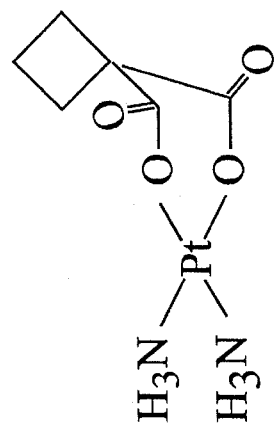
Figure 2:
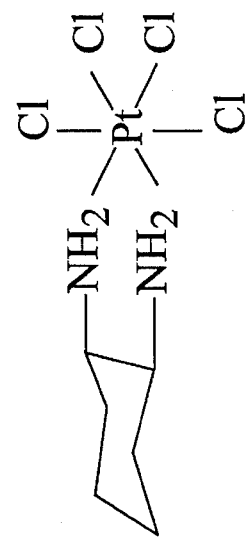
Figure 2:
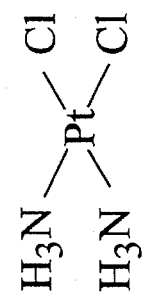
Figure 2:
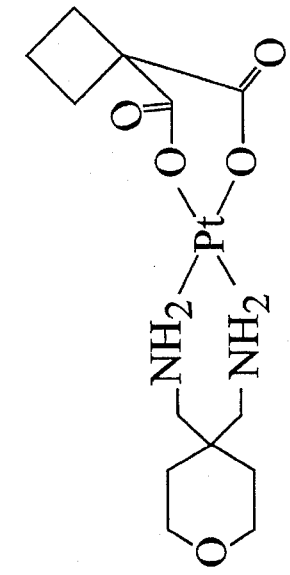

$^{13}C$, $^{195}Pt$ and $^{199}Hg$ NMR are all consistent with the assigned structure of the cross-linker complex (see FIG. 1 ). In the case of the $^{13}C$ spectrum shown in FIG. 5, the low signal to noise level is due to the fact that the complex reacts with the solvent, and consequently the acquisition time is limited before product peaks begin to grow into the spectrum. (In order to circumvent this problem to some extent, the spectrum was acquired using a pulse delay of 0.5 sec, instead of the more usual 4 second delay used for typical $^{13}C$ NMR spectroscopy.) The NMR spectral data for are collected in Table 1, below, with $^{195}Pt$ and $^{199}Hg$ chemical shift values of related complexes listed for comparison. Since both $^{195}Pt$ and $^{199}Hg$ are readily detectable spin ½ nuclei, characterization of the metal environments is facilitated, as the complex gives spectra which correspond well with values obtained for analogous compounds.

TABLE I

NMR Spectral Data for Products of Steps 8 and 9

| Nucleus | Complex | Solvent | δ (ppm) | Ref |
|---|---|---|---|---|
| $^1H$ | 9 | DMSO | 1.45–1.75, 2.11, 2.33, 2.58 5.03, 5.24, 5.35, 5.50 | a |
|  | 8 | $D_2O$ | 1.55–1.8, 1.89, 2.58, 2.87 3.08, 3.38 | a |
| $^{13}C$ | 9 | DMSO | 25.75, 30.73, 35.03, 52.24 60.11 | a |
|  | 8 | $D_2O$ | 25.9, 26.1, 30.4, 36.1, 36.2 44.2, 51.7, 51.8, 60.1, 60.3 | a |
| $^{195}Pt$ | 9 | NMP | −2263 | a |
|  | 9 | DMSO | −2283 | a |

TABLE I-continued

NMR Spectral Data for Products of Steps 8 and 9

| Nucleus | Complex | Solvent | δ (ppm) | Ref |
|---|---|---|---|---|
| | 8 | $D_2O$ | −3255, −3261 | a |
| | $PtenCl_2$ | DMF | −2317 | b |
| | cis-DDP | DMSO | −2087 | c |
| | [PtenCl-(DMSO)]Cl | $D_2O$ | −3296 | a |
| $^{199}Hg$ | 9 | NMP | −988 | a |
| | 8 | $D_2O$ | −1006 | a |
| | $CH_3HgCl$ | NMP | −835 | a |
| | $CH_3HgCl$ | DMSO | −874 | a |

Solubility of the Cross-Linker Complex

As prepared by the method described in Example 1, the complex dissolves sparingly in amide solvents. However, dissolution in DMSO followed by immediate precipitation with ethanol renders the complex readily soluble in NMP. This appears to be an effect of particle size on dissolution rate, since no differences can be discerned in the infrared spectra of the complex before or after this treatment. In particular there is no evidence for coordinated DMSO in the region 1000–1200 cm$^{-1}$.

The Fast Atom Bombardment Mass Spectrometry (FAB-MS) of a sample of the complex dissolved in DMSO immediately prior to running the spectrum shows the parent ion at M/e=645, corresponding to [M+DMSO−Cl]. UV spectroscopic studies have shown that the kinetics of the reaction of the complex with DMSO are in accord with the published rate data for reaction of cis-Pt(NH$_3$)$_2$Cl$_2$ with DMSO. At room temperature, this corresponds to a half-life of approximately 3 hours, and it is not expected that sufficient platinum-DMSO complex will be produced over the course of a few minutes' sample preparation time to give rise to the observed mass spectrum. Thus, the organomercurial complex appears to react with DMSO to generate an adduct which is sufficiently stable to give rise to a peak in the mass spectrum, but which is disrupted on precipitation. This conclusion is also borne out by the observation that an independent attempt to prepare the DMSO adduct of MeHgCl by dissolution in DMSO and precipitation with diethyl ether resulted in recovery of the starting mercurial chloride.

EXAMPLE 4

Characterization of Intermediate Species

NMR spectral data for the product of Step 8 are presented in FIGS. 6–7. The spectra are in good agreement with the proposed structure, and show clear evidence that the complex is formed as a pair of isomers, as demonstrated by the presence of closely spaced pairs of resonances in the $^{13}C$ and $^{195}Pt$ spectra. The proton-coupled $^{199}Hg$ NMR spectrum shows a pattern of five peaks spaced apart by approximately 225 Hz. This is consistent with the proton spectra of organomercurial complexes such as ClH$_3$N(CH$_2$)$_3$HgCl, which exhibit $^{199}Hg$ satellites with coupling constants of this magnitude.

For ClH$_3$N(CH$_2$)$_3$HgCl, coupling is observed to the protons at the positions α- and β- to the mercury atom In this case $^2J_{HG-H}$=220 Hz, and $^3J$=232 Hz. The coupling pattern observed in the $^{199}Hg$ NMR spectrum of the final merplatin cross-linker complex is therefore attributed to splitting of the $^{199}Hg$ signal by the two a-protons to give rise to a triplet coupling pattern with $^2J_{HG-H}$~220 Hz, which is then further split by the β-protons to result in an overlapping triplet of triplets. Because of the similarity in the coupling constants, the nine possible signals overlap to give rise to a spectrum which appears to be caused by splitting of the $^{199}Hg$ resonance by four equivalent protons, resulting in a five-line pattern with an apparent $J_{HG-H}$ that is intermediate between the two contributing coupling constants.

EXAMPLE 5

Preparation of Cross-Linker Species with Alternative Linking Chain Length

As mentioned above, the preparative scheme for the crosslinker species of the present invention has been designed to readily accomodate the incorporation of aliphatic linking chains of varying lengths to achieve a range of inter-metal distances in the complex. A multi-step synthesis of a cross-linker species with a five-carbon linking entity is presented below.

Step 1: Preparation of 2-(diphenylmethylimino)-6-heptenenitrile

A 12.0 g sample (54.4 mmol) of 2-(diphenylmethylimino)acetonitrile was dissolved in 70 mL of dichloromethane. A 1.3 g sample (5.3 mmol) of benzyltriethylammoniumchloride and 15 mL 50% NaOH were added to the ice-cooled solution. Over a period of 2 hours, 13.2 g of 5-bromo 1-pentene (88.6 mmol) was slowly added under vigorous stirring. The mixture was stirred for another 22 hours, which was interrupted by addition of two 5-mL portions of 50% NaOH after 4 hours and 20 hours. The dark red mixture was then poured into a separatory funnel containing 100 mL of water and 100 mL of dichloromethane. The aqueous layer was extracted with three 50-mL portions of dichloromethane. The organic layer was then washed with two 50-mL portions of water, and finally with 50 mL of a saturated sodium chloride solution. After removal of the solvent and drying over magnesium sulfate, the crude product was purified by carrying out a Kugelrohr distillation, yielding 10.2 of product (56% yield).

[characterization: $^1$H-NMR (CDCl$_3$): δ=1.54 (m, 2H); δ=2.01 (m, 4H); δ=4.23 (m, 1H); δ=4.93 (m, 2H); δ=5.72 (m, 1H); δ=7.50 (m, 10H)]

Step 2 Preparation of 2-amino-6-heptenenitrile hydrochloride.

A 10.0 g sample (34.7 mmol) of the product of Step 1 (2-(diphenylmethylimino)-6-heptenenitrile) was dissolved in 100 mL of pentane and stirred for 18 hours with 100 mL of a 1N HCl solution. The aqueous layer was extracted with two 50-mL portions of pentane, and then evaporated to dryness under reduced pressure. The white-yellow residue was taken up in 10 mL of methanol and, after stirring with 200 mL of ether, a white product could be isolated, at a yield of 4.5 g (74% yield).

[characterization: $^1$H-NMR (D$_2$O); δ=1.48 (m, 2H); δ=1.84 (m, 2H); δ=1.99 (m, 2H); δ=4.36 (m, 1H); δ=4.90 (m, 2H); δ=5.68 (m, 1H).]

Step 3 Preparation of 1,2-di-(N-t-butoxycarbonylamino)-6-heptene.

A 3.2 gram sample (19.9 mmol) of the product of Step 2 (2-amino-6-heptenenitrile hydrochloride) were suspended in 30 mL of dry tetrahydrofuran (THF) and 50 mL of 1M lithium aluminium hydride in THF was added over a period of 30 minutes under an inert gas atmosphere, creating a slightly yellow-colored solution. After additional stirring for 90 minutes at room temperature, 50 mL of water were carefully added with cooling by ice. To the resulting white suspension (aluminium hydroxide), 4.3 mL of triethylamine and 4.7 g of BOC$_2$O (21.5 mmol) were added, and stirring was continued at room temperature for 90 minutes. After removal of the THF under reduced pressure, the suspension was acidifed with potassium hydrogen sulfate solution. The mixture was extracted with three 50-mL portions of ether. The ether solution was washed with three 50-mL portions of water, and dried over magnesium sulfate. After evaporation to dryness, the crude product was recrystallized from hexane, yielding 3.3 grams of product (52% yield).

Step 4 Preparation of 1,2-diamino-7-chloromercuriheptane dichloride.

A 3.0 gram sample (9.39 mmol) of the product of the previous Step (1,2-di-(N-t-butoxycarbonylamino)-6-heptene was dissolved in 10 mL of THF, and 19 mL of a 0.5M solution of 9-BBN was added with ice cooling over a period of 15 minutes under an inert gas atmosphere. After stirring at room temperature for 1 hour, 3.0 grams of Hg(OAc)$_2$ (9.43 mmol) were added, causing a grey suspension which turns to an almost colorless solution after 30 minutes. The solution was then poured into 250 mL of ice water containing 1.16 g of sodium chloride (20 mmol). The suspension was extracted with three 50mL portions of dichloromethane. After drying over magnesium sulfate, the organic phase is reduced to a volume of 50 ml, and a slow stream of HCl gas is bubbled through the solution for 30 minutes. The white precipitate was collected, washed with dichloromethane and ether, yielding 2.3 g of product (56% yield).

Step 5 Preparation of 1,2-diamino-7-chloromercuriheptane sulfate

The chloride salt of the product of Step 4 was converted to the sulfate by suspending a 0.68 g sample in 5 mL of water. To the filtrate, 10 drops of concentrated sulfuric acid were added and addition of 50 mL of ethanol caused the formation of the pure sulfate, yielding 0.47 g of product (65% yield).

[characterization: $^1$H-NMR (D$_2$O); δ=1.42 (m, 4H); δ=1.70 (m, 4H); δ=2.00 (m, 2H); δ=3.28 (d, 2H); δ=3.58 (m, 1H)]

Step 6 Preparation of (7-chloromercuri-1,2-heptanediamine)dichloroplatinum(II).

A 1.80 gram sample (0.39 mmol) of the product of Step 5 (1,2-diamino-7-chloromercuriheptane sulfate) were suspended in 10 mL of water. After addition of 0.15 mL of triethylamine and 164 mg of (DMSO)$_2$PtCl$_2$ (0.39 mmol), the reaction mixture is stirred for 1 hour at room temperature until the Pt starting complex had disappeared. Then, 15 mL of 0.5N HCl were added, and a small amount of insoluble material was removed by filtration. After stirring for 48 hour at 50° C., a yellow precipitate could be collected which was washed with water, ethanol and ether, yielding 160 mg of product (65% yield).

Step 7 Purification of (7-chloromercuri-1,2- heptanediamine)dichloroplatinum(II).

A suspension of the product of Step 6 (80 mg, 0. 13 mmol) and silver nitrate (48 mg, 0.28 mmol) in 10 mL of water was stirred at room temperature in the dark for 4 days. To the filtrate, 20 mg of potassium chloride were added, and after 2 hours, the yellow product was collected and washed with ethanol and ether, yielding 53 mg of product (91% yield).

[Analysis Calculated for C$_7$H$_{17}$N$_2$Cl$_3$Pt Hg: C 13.32%, H 2.72%, N 4.44%; found: C 13.82%, H 2.78%, N 4.53%]

EXAMPLE 6

In Vitro Assays of Cross-Linking

The activity of the reagent in forming reversible DNA-protein crosslinks has been demonstrated using an in vitro assay based on the gel mobility-shift effect (FIGS. 8–11). (Pried & Crothers, 1981; Garner & Revsin, 1981).

Materials and Methods

Proteins and DNA Probes. TFIIIA from *Xenopus Borealis* was provided by T. Tullius (Johns Hopkins University) and A. Wolffe (NIH). Fur was purified based on the method of Neilands and coworkers. MerR extract was obtained and quantified as described (O'Halloran, 1989). DNA probes used in TFIIIA, Fur, and MerR gel mobility shift assays were derived from plasmids pXBS201 (obtained from T. Tullius), pGMer and pBIB, respectively. The 249-bp BamHI-HindIII fragment from pXBS201, 309-bp XhoI-PvuII fragment from pBIB and 411-bp BssHII-BssHII fragment from pGMer are labeled with [α-$^{32}$P]dNTPs (Amersham) by the Klenow fragment of DNA polymerase (Bethesda Research Laboratories). The labeled fragments are then isolated and purified by gel electrophoresis. DNA concentrations were determined by optical density at 260 nm by using a molar extinction coefficient of $1.3 \times 10^4$ per nucleotide pair.

Preparation of Cold Competitor by PCR. The plasmid pGTFA was constructed by cutting the 249-bp BamHI-HindIII fragment which contains the TFIIIA binding site and then inserting into the vector pGEM1 (Promega). The pGTFA, pBIB and pGMer were then used as templates in the PCR reaction to get large amounts of fragments containing TFIIIA, Fur or MerR binding sites. The plasmid was mixed in a final volume of 100 μL reaction buffer to give a final concentration of 50 mM KCl, 1.5 mM MgCl$_2$, 10 mM Tris-HCl (pH 8.3), 0.2 mM dNTPs each, 50 pmol of each primer, 2.5 U AmiliTaq DNA polymerase (Cetus or Phamacia) and then subjected to 30 cycles of amplification in a Perkin Elmer-Cetus thermal cycler. Thermal cycling conditions were 1 min at 94° C. (denaturation), 2 min at 55° C. (annealing) and 3 min at 72° C. (extension). Amplification was completed by a final incubation at 72° C. for 10 min. After checking on the 1% mini agarose gel, these PCR products are directly used as cold competitors in the crosslinking assays.

Crosslinker. The crosslinker was designed as described above. The 10 mM stock was made by dissolving 1 mg crosslinker into 166 μDimethyl Sulfoxide (DMSO) (Mallinckrodt) quickly and then was stored in the −20° freezer. This stock lasts for approximately two months. Therefore, a small aliquot was taken to make a series of dilutions each time immediately before the reaction. The DMSO or the binding buffers were used as solvent for dilution.

Crosslinking Activity Assay. DNA-protein-crosslinker are incubated in 20 μl (final volume) of binding buffer. The buffer for TFIIIA and MerR extract reaction is 20 mM Hepes [pH 7.5], 50 mM K$_2$SO$_4$, 10 μMZnsO$_4$, 3 mM MgCl$_2$, 10% glycerol and 70 μg/ml Albumin, Bovine-carboxymethyl [c-BSA] (Sigma). The Fur incubation buffer is 20 mM Bis-Tris/Borate [pH 7.0], 50 mM K$_2$SO$_4$, 5% glycerol, 1 mM MgCl$_2$, 5 μG/ml salmon sperm DNA and 100 μg/ml c-BSA. In the experiment of TFIIIA and Fur, the protein-DNA-crosslinker complex was incubated at room temperature for 3 hr. while in the case of MerR extract assay, the complex was formed at 37° C. for 1.5 hr. For the competition, a large excess of unlabeled specific DNA (cold competitor) was then added to this complex and were incubated another 45 min. at 37° C. prior to gel separation. Reversal of the crosslinks was performed by addition of 25 mM KCN (pH8) (Aldrich Chemical Company) per reaction to the crosslinked complex prior to competition. The gel for TFIIIA assay is a 5% polyacrylamide (30:1) in HE (10mM Hepes [pH 8.3], 0.1 mM EDTA) buffer and run at 180 V for 2 hours and Fur experiments were carried out with 5% polyacrylamide gel (30:0.8)in Bis-Tris/Borate (7.0) buffer at 180 V for 2.5 hr in MerR crude extract assay, samples were loated on to a 10% polyacrylamide (75:1) HE gel and electrophoresed at 200 V for 3.5 hr. The gel was then dried under vacuum and subjected to autoradiography.

CROSSLINKING ASSAYS

Crosslinking of MerR

Samples of the 411 bp BSSH II fragment of the plasmid pGMER, radiolabelled at the 5' termini (400 disintegrations per minute, [DNA]=approximately 100 pM fragment) were incubated with MerR protein in binding buffer (20mM HEPES, pH 7.5, 50 mM $K_2SO_4$, 5% glycerol, 70 μg ml$^{-1}$ carboxymethyl-BSA, 7 mM MgCl2, 10 μM $ZnCl_2$) for 30 minutes at 37° C. Crosslinker (or metal control) solutions were then added, and the samples incubated for three hours at 37° C. After this time, the relevant samples were treated with sodium cyanide, and incubated a further 20 minutes. Finally, competitor DNA (10 nM final concentration) was added, and the samples were incubated an additional 30 minutes. The samples were then electrophoresed at 200 V on a non-denaturing polyacrylamide gel (10%, 75:1 acrylamide:bis-acrylamide) for 3 hours, transferred to paper, dried, and exposed overnight to X-ray film at −70° C. with an intensifying screen before development.

Crosslinking of TFIIIA 400 cpm of the 249 bp BSSHII-EcoR1 fragment of the plasmid pXBS201 [62] was incubated with TFIIIA, and various concentrations of the crosslinker in binding buffer (20 mM HEPES, pH 7.5, 50 mM $K_2SO_4$, 5% glycerol, 70 μG ml-$^1$ carboxymethyl-BSA, 7 mM $MgCl_2$, 10 μM $ZnCl_2$) for 2.5 hr at 37° C. Reversing agent was then added, and the samples were incubated for a further 40 minutes. Unlabelled DNA was added, and the competition reaction was allowed to run for a further hour. Loading dye (50% glycerol, 0.03% bromophenol blue, 0.03% xylene cyanol) was added to each reaction, the samples were loaded onto a 8% polyacrylamide gel, (30:1 acrylamide: bis-acrylamide) and electrophoresed at 200 V for 2 hr. The dried gels were exposed to Kodak X-OMAT film overnight at −70° C., with the use of an intensifier screen, and developed.

RESULTS

The assay used to determine the DNA-binding activity of the complexes is based on the assays developed by Lippard and coworkers for assaying the extent of DNA binding by cis-DDP, in which the electrophoretic mobility of a DNA molecule is altered by binding of the drug (Sundquist, 1990). Charge neutralization and DNA bending caused by binding of the divalent metal complex have been invoked to explain the observed mobility shift. Whereas the reported assays were carried out using agarose gel electrophoresis of whole plasmid DNA, it was found to be more expedient to conduct the assay using polyacrylamide gel electrophoresis of a radiolabelled DNA fragment. As shown in FIGS. 8 to 11, electrophoresis of DNA treated with increasing concentrations of the crosslinker complex results in a saturation binding curve which is identical in form with a curve obtained by incubation of DNA with $PtenCl_2$. Conversely, DNA incubated with MeHgCl does not exhibit a mobility shift at all, indicating that the platinum portion of the molecule is solely reponsible for causing the DNA mobility shift observd.

EXAMPLE 6

Variation of the Preparative Scheme to Alter Metal-to-Metal Distances

As discussed above, it is possible to prepare a series of crosslinker molecules in which the intermetal spacing is varied in a systematic fashion to allow assessment of the importance of the distance between metal ions in the crosslinking reaction. The synthetic scheme devised for the cross-linker reagent of FIG. 1 was specifically designed to allow for ready modification of the scheme to give the desired chain length between the metal ions, by substitution of longer chain bromoalkenes for allyl bromide in the phase-transfer alkylation step. The alkylation has been shown to proceed smoothly and in high yield with 5-bromo-1-pentene, supporting the principle that such a modification of the synthetic protocol should yield a homologous series of crosslinker molecules. Using the molecular modelling program Chem3D (Cambridge Scientific Computing, Inc., Cambridge, Mass.), the approximate intermetal distances in the series has been determined. These are listed in the table below as intermetal spacing versus carbon chain length of alkyl bromide used in the alkylation step, demonstrating that the addition of each —$CH_2$ group into the alkyl chain results in an increase in intermetal spacing of 1.2 to 1.3 Å.

| n | Hg—Pt distance (Å) |
| --- | --- |
| 1 | 8.1 |
| 2 | 9.2 |
| 3 | 10.4 |
| 4 | 11.6 |
| 5 | 12.9 |

EXAMPLE 7

Preparation of Cross-Linking Reagents with Alternative DNA-binding Moieties

Substitution of other DNA-binding moieties for the cisplatin-based reagent of FIG. 1 would allow variation of the DNA-sequence preferences of the crosslinker. One possible variation would be to couple an organomercurial to the DNA intercalator molecule psoralen. Psoralens are a family of compounds which are capable of intercalating into DNA and undergoing photochemically initiated reactions leading to the formation of covalent adducts with the DNA (Vigny et al, 1985). Coupling of a psoralen derivative to an organomercurial would therefore result in a hybrid photoactivatible crosslinker, with a strong preference for AT-rich sequences on DNA. (Boyer et al, 1988).

Preparation of the reagent as outlined in the scheme of FIG. 12, as would be recognized by one of skill in the relevant chemical arts, would be straightforward, beginning with commercially-available 8-methoxpsoralen (Sigma). Demethylation and alkylation of the compound have been reported previously (Begley, T. Ph.D. Dissertation, 1983, California Insitute of Technology). The incorporation of mercury into the molecule is expected to be straightforward: use of the sterically hindered 9-borabicyclo[3.3.1]nonane (9-BBN) will strongly favor addition to the terminal alkene in the hydroboration step (Brown, 1970), and is not expected to reduce any of the double bonds in the aromatic system. Treatment of the intermediate alkylborane is expected to yield the product shown in FIG. 12. A possible side reaction may be addition of mercuric acetate across the electron-rich double bond of the furan ring: however this reaction is easy to detect due to the $^{199}$Hg-$^1$H couplings observed in the $^1$H NMR spectrum of the product. Should this reaction be observed, adjustment of the reaction conditions to yield the desired product would not be difficult, since the mechanism of the boron/mercury exchange reaction proceeds via a concerted mechanism between the alkylborane and Hg(OAc)$_2$ (Abraham & Dadjour, 1974), while acetoxymercuration of alkenes involves attack of the alkene by Hg(OAc)$^+$ (Bloodworth, 1977). Addition of a reagent such as sodium acetate, which suppresses dissociation of the mercuric diacetate in THF solution would thus favor the exchange reaction.

Because numerous modifications and variations in the practice of the present invention are expected to occur to those skilled in the art, only such limitations as appear in the appended claims should be placed thereon.

REFERENCE LIST

The references listed below are incorporated herein by reference to the extent that they supplement, explain, provide a background for, or teach methodology, techniques, and/or compositions employed herein.

Abraham & Dadjour, (1974) *J. Chem. Soc. Perkin II*, 233.
Bancroft et al., (1990) *J. Am. Chem. Soc.*, 112:6860.
Begley, T. Ph.D. Dissertation, 1983, California Insitute of Technology
Berg, & Lippard, (1989), *Progress in Inorganic Chemistry*, Ed. (Wiley, New York), 37:143.
Berg, JM, (1989) *Met. Ions Biol. Syst.*, (John Wiley & Sons, New York), 235–254.
Bloodworth, A J, in *The Chemistry of Mercury*, McAuliffe, C. A., Ed., Toronto: MacMillan of Canada, 1977, p. 168
Boyer et al., (1988) *Biochemistry*, 27:3011–18.
Brown et al., (1970) *J. Am. Chem. Soc.*, 96:7765.
Chu & Orgel, (1992) *Nucleic Acids Research*, 20:2497–2502.
Ciccarelli et al., (1985) *J. Biochemistry*, 24:7533–40.
Coleman, J E, (1992) *Annu. Rev. Biochem.*, 61:897
Falchuck et al., In *The Chemistry of Mercury*; C. A. McAuliffe,, Ed.; MacMillan of Canada: Toronto, Canada, 1977; Vol. Part 4; p 261–285.
Farrell, N., in *Platinu, Gold and other Metal Chemotherapeutic Agents* (Ed. Lippard) (American Chemical Soceity Symposium Series, Washington, D.C. 1983).
Frantz & O'Halloran, (1990) *Biochemistry* 29:4747.
Garner & Revsin, (1981) *Nucl. Acids. Res.*, 9:6505–6525.
Heltzel et al., (1990) *Biochemistry* 29:9572.
Harrison, S C, (1991) *Nature* 353:715.
Hollis et al., (1991) *Cancer Res.*, 51:1866–75.
Hollis et al., (1989) *J. Med. Chem.*, 32:128–36.
Kauffman, G B, in J. Kleinberg (Ed.), *Inorganic Synthesis*, McGraw-Hill Book Co., Inc. New York, 1963.
Klug, A, (1989) *S. Afr. J. Sci.*, 85:576–81.
Miller et al., (1985) *EMBO J.* 4:1609.
O'Donnell et al., (1989) *J. Am. Chem. Soc.*, 111:2353–2355.
O'Donnell & Eckrich, (1978) *Tett. Lett.*, 47:4625.
O'Donnell & Polt, (1982) *J. Org. Chem.*, 47:2663–2666.
O'Halloran, (1989) *Metal Ions in Biological Systems*, (Marcel Dekker, Inc., New York) 105–146.
Pil & Lippard, (1992) *Science* 256:234.
Pried & Crothers, (1981) *Nuc. Acids Res.*, 9:6505–6525.
Rabenstein & Reid, (1984) *Inorg. Chem.*, 23:1246–50.
Ralston & O'Halloran, (1990) *Proc. Nat'l Acad. Sci. U.S.A.* 87:3846.
Rebek & Nemeth, (1985) *J. Am. Chem. Soc.*, 107:6738–6739.
Rhodes & Klug, (1993) *Sci. Am.* 269:56.
Rosenberg et al., (1965) *Nature* 205:698.
Sherman & Lippard, (1987) *J. Chem. Rev.*, 87:1153–1181.
Sundquist et al., (1987) *J. Am. Chem. Soc.*, 26:1524–1528.
Sundquist & Lippard, (1990) *Coord. Chem. Rev.* 100:293.
Thiele, D J, (1988) *Mol. Cell Biol.*, 8:2745–2752.
Vallee & Falchuk, (1992) *Physiol. Rev.*, 73:79.
Vigny et al., (1985) *J. Biochimie*, 67:317.
Waters et al., (1978) *J. Raman Spec.*, 7:288–293.
Watton et al., (1990) *J. Am. Chem. Soc.* 112:2824.
Welch et al., (1989) *EMBO J.*, 8:225–260
Wright et al., in *Progress in Inorg. Chem.*, S. Lipard, Ed., New York: Wiley & Sons, 1990

What is claimed is:

1. A bi-metallic cross-linking reagent according to the following formula:

$$\begin{array}{c} L_3 \quad L_4 \quad NH_2 \\ \diagdown \mid \diagup \\ M_1 \\ \diagup \mid \diagdown \\ L_2 \quad L_1 \quad NH_2 \end{array} \diagdown (CH_2)_n - M_2 - L_5$$

wherein $M_1$ is a metal ion species capable of forming a complex of coordination number four or coordination number six;

wherein $L_1$, $L_2$, $L_3$, and $L_4$ are each independently a halide, ammonia, dimethyl sulfoxide, carboxylate, thiolate, imidazole, a nucleobase, or an empty coordination site, provided that no more than two of $L_1$, $L_2$, $L_3$, and $L_4$, are empty coordination sites;

wherein $M_2$ is a metal ion species capable of forming a complex of coordination number two with a first ligand that is a hydrocarbon moiety and a second ligand that is kinetically labile;

wherein $L_5$ is a ligand that forms a kinetically labile coordination bond with $M_2$; and wherein n is an integer from two to nine.

2. The cross-linking reagent of claim 1, wherein $M_1$ is platinum, ruthenium, palladium or nickel.

3. The cross-linking reagent of claim 1, wherein up to three of $L_1$, $L_2$, $L_3$, $L_4$ and $L_5$ are each a halide.

4. The cross-linking reagent of claim 3, wherein up to three of $L_1$, $L_2$, $L_3$, $L_4$ and $L_5$ are each chloride.

5. The cross-linking reagent of claim 1, wherein $M_1$ is platinum(II), and up to two of $L_1$, $L_2$, $L_3$ and $L_4$ are empty coordination sites.

6. The cross-linking reagent of claim 1, wherein $M_1$ is platinum(IV), and none of $L_1$, $L_2$, $L_3$ and $L_4$ are empty coordination sites.

7. The cross-linking reagent of claim 1, wherein $M_2$ is mercury(II).

8. The cross-linking reagent of claim 1, wherein n is an integer from three to five.

9. The cross-linking reagent of claim 8, wherein n is three.

10. The cross-linking reagent of claim 8, wherein n is five.

11. A bi-metallic nucleotide/peptide cross-linking reagent according to the following formula:

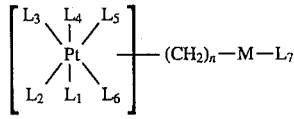

wherein $L_1$ to $L_6$ are each independently amine, a halide, cyclohexylamine, carboxylato, or empty coordination sites, provided that no more than two of $L_1$–$L_4$ are empty coordination sites;

wherein any two of $L_1$ to $L_6$ are together cyclobutane-1,1-dicarboxylato-O,O', tetrahydro-4H-pyran-4,4-dimethanamine-N,N', 1,2-diaminecyclohexane-N,N', or 2,2-bis(aminomethyl)-1,3-propanediol;

wherein M is a metal ion species capable of forming a complex of coordination number two with a first ligand that is a hydrocarbon moiety and a second ligand that is kinetically labile;

wherein $L_7$ is a ligand that forms a kinetically labile coordination bond with M; and wherein n is an integer from 2 to 9.

12. The cross-linking reagent of claim 11, wherein M is mercury(II).

13. The cross-linking reagent of claim 11, wherein n is an integer from three to five.

14. A method for reversibly linking a first molecule to a second molecule, comprising the steps of:

(a) reacting the first molecule with the bi-metallic cross-linking reagent of claim 1 under conditions effective to bind a first metal ion center of the bi-metallic reagent to the molecule; and (b) reacting the product of part (a) with the second molecule under conditions effective to bind a second metal ion center of the bi-metallic reagent to the molecule.

15. The method of claim 14, wherein the first molecule is a polynucleotide.

16. The method of claim 14, wherein the second molecule is a protein, a peptide, or a molecule having a thiol moiety.

17. The method of claim 16 wherein the protein is a metalloregulatory protein.

18. The method of claim 16, wherein the protein has a zinc finger motif.

19. The method of claim 16, wherein the protein is MerR, Fur, GAL4, or TFIIIA.

20. The method of claim 16, wherein the molecule having the thiol moiety is a thioether or a phosphothiolate.

21. The method of claim 16, wherein the molecule having the thiol moiety is hexestrol.

22. A linked species wherein a first molecule is linked to a second molecule through the bi-metallic cross-linking reagent of claim 1, wherein the linked species is prepared by the process of:

(a) reacting the first molecule with the bi-metallic cross-linking reagent of claim 1 under conditions effective to bind a first metal ion center of the bi-metallic reagent to the molecule; and (b) reacting the product of part (a) with the second molecule under conditions effective to bind a second metal ion center of the bi-metallic reagent to the molecule.

23. A linked species wherein a first molecule is linked to a second molecule through the bi-metallic cross-linking reagent of claim 1, wherein the linked species is prepared by the process of:

(a) reacting the first molecule with the bi-metallic cross-linking reagent of claim 1 under conditions effective to bind a first metal ion center of the bi-metallic reagent to the molecule; and (b) reacting the product of part (a) with the second molecule under conditions effective to bind a second metal ion center of the bi-metallic reagent to the molecule.

24. The linked species of claim 23, wherein $M_1$ is platinum(II), $M_2$ is mercury(II), $L_2$, $L_3$, and $L_5$ are each chloride, and wherein n is three or five.

25. The linked species of claim 24, wherein the second molecule is a polynucleotide.

26. The linked species of claim 24, wherein the first molecule is a protein, a peptide, or a molecule having a thiol moiety.

27. The linked DNA-protein species of claim 26, wherein the protein is MerR, Fur, GAL4, or TFIIIA.

28. A linked species comprising a cell-specific molecule and the bi-metallic cross-linking reagent of claim 1.

29. The linked species of claim 28, wherein a first metal center of the bi-metallic cross-linking reagent is linked to the cell-specific molecule and a second metal center of the cross-linking reagent comprises an anti-tumor agent.

30. The linked species of claim 29 wherein the antitumor agent is selected from the group consisting of cisplatin, carboplatin, JM-216, tetraplatin, zeriplatin, and enloplatin.

31. The linked species of claim 29 wherein the cell-specific molecule is a cell surface receptor or a nuclear receptor.

32. A method of delivering an anti-tumor agent to a cell wherein a specific cell type is targeted for delivery of the agent, the method comprising the step of administering the linked species of claim 29.

* * * * *

UNITED STATES PATENT AND TRADEMARK OFFICE
CERTIFICATE OF CORRECTION

PATENT NO. : 5,534,542
DATED : July 9, 1996
INVENTOR(S) : Thomas V. O'Halloran, et. al.

It is certified that error appears in the above-indentified patent and that said Letters Patent is hereby corrected as shown below:

At column 1, line 3, insert --The government owns rights in the present invention pursuant to NIH Grant RO1GM45972--.

In Claim 1, Column 28, Line 61; Claim 8, Column 29, Line 9; Claim 9, Column 29, Line 11; Claim 10, Column 29, Line 12; Claim 11, Column 29, Line 34; Claim 13, Column 29, Line 37; and Claim 24, Column 30, Line 33, delete "n" and substitute --n-- therefor.

In Claim 30, Column 30, Line 47, delete "antitumor" and substitute --anti-tumor-- therefore.

Signed and Sealed this

Third Day of December, 1996

*Attest:*

BRUCE LEHMAN

*Attesting Officer*       Commissioner of Patents and Trademarks